United States Patent
Gründeman et al.

(10) Patent No.: US 11,376,123 B2
(45) Date of Patent: *Jul. 5, 2022

(54) PROSTHETIC VALVE AND METHOD OF MAKING A PROSTHETIC VALVE

(71) Applicant: DSM IP ASSETS B.V., Heerlen (NL)

(72) Inventors: Paul Frederik Gründeman, Utrecht (NL); Jolanda Kluin, Utrecht (NL); Karlien Kristal Boon-Ceelen, Echt (NL); Thomas König, Utrecht (NL)

(73) Assignee: DSM IP ASSETS B.V., Heerlen (NL)

( * ) Notice: Subject to any disclaimer, the term of this patent is extended or adjusted under 35 U.S.C. 154(b) by 177 days.

This patent is subject to a terminal disclaimer.

(21) Appl. No.: 16/702,458

(22) Filed: Dec. 3, 2019

(65) Prior Publication Data

US 2020/0107928 A1    Apr. 9, 2020

Related U.S. Application Data

(63) Continuation of application No. 15/857,359, filed on Dec. 28, 2017, now Pat. No. 10,524,902, which is a
(Continued)

(30) Foreign Application Priority Data

May 6, 2014  (EP) .................................. 14167269
May 6, 2014  (EP) .................................. 14167270
(Continued)

(51) Int. Cl.
*A61F 2/24* (2006.01)

(52) U.S. Cl.
CPC .......... *A61F 2/2418* (2013.01); *A61F 2/2412* (2013.01); *A61F 2/2415* (2013.01); *A61F 2220/0075* (2013.01)

(58) Field of Classification Search
CPC ......... A61F 2/24; A61F 2/2418; A61F 2/2448
(Continued)

(56) References Cited

U.S. PATENT DOCUMENTS 3,526,906 A    9/1970  DeLaszlo
3,859,668 A    1/1975  Anderson
(Continued)

FOREIGN PATENT DOCUMENTS

EP    0 269 151    10/1987
EP    0 269 151    6/1988
(Continued)

OTHER PUBLICATIONS

Hasan et al, "Biomechanical properties of native and tissue engineered heart valve constructs," Journal of Biomechanics 47 (2014) 1949-1963.
(Continued)

*Primary Examiner* — Suzette J Gherbi
(74) *Attorney, Agent, or Firm* — Nixon & Vanderhye P.C.

(57) ABSTRACT

Prosthetic valves are provided with a leaflet assembly having at least one leaflet attached to a supporting element, which leaflet has a free margin that can move between a first position wherein the free margin is flexed away from a closure surface to allow body fluid to flow through the valve, and a second position wherein the free margin abuts the closure surface to close the valve, and wherein the leaflet, without pulsatile load on the valve, can form a coaptation height H of more than 0.1 mm along the length of the free margin. Such prosthetic valve provides good performance during prolonged time, and can be made using various materials for the leaflets.

21 Claims, 12 Drawing Sheets

Related U.S. Application Data continuation of application No. 15/308,981, filed as application No. PCT/EP2015/059982 on May 6, 2015, now Pat. No. 10,039,640.

(30) Foreign Application Priority Data

| May 6, 2014 | (EP) | .................................... | 14167271 |
| May 6, 2014 | (EP) | .................................... | 14167272 |

(58) Field of Classification Search
USPC ................................................ 623/2.1–2.19
See application file for complete search history.

(56) References Cited

U.S. PATENT DOCUMENTS

| 4,035,849 | A | 7/1977 | Angell et al. |
| 4,191,218 | A | 3/1980 | Clark et al. |
| 4,222,126 | A | 9/1980 | Boretos et al. |
| 4,364,127 | A | 12/1982 | Pierce et al. |
| 4,610,688 | A | 9/1986 | Silvestrini et al. |
| 4,731,074 | A | 3/1988 | Rousseau et al. |
| 5,500,014 | A | 3/1996 | Quijano et al. |
| 5,509,930 | A | 4/1996 | Love |
| 5,800,514 | A | 9/1998 | Nunez et al. |
| 5,855,602 | A | 1/1999 | Angell |
| 5,861,028 | A | 1/1999 | Angell |
| 6,171,335 | B1 | 1/2001 | Wheatley et al. |
| 6,283,995 | B1 | 9/2001 | Moe et al. |
| 6,454,799 | B1 | 9/2002 | Schreck |
| 6,726,715 | B2 | 4/2004 | Sutherland |
| 7,465,316 | B2 | 12/2008 | Kujawski |
| 8,043,551 | B2 | 10/2011 | Heim et al. |
| 10,039,640 | B2 * | 8/2018 | Grundeman .......... A61F 2/2412 |
| 2003/0097175 | A1 | 5/2003 | O'Connor et al. |
| 2003/0114924 | A1 | 6/2003 | Moe |
| 2004/0176658 | A1 | 9/2004 | McMurray |
| 2005/0027348 | A1 | 2/2005 | Case et al. |
| 2005/0137681 | A1 | 6/2005 | Shoemaker et al. |
| 2005/0149118 | A1 | 7/2005 | Koyfman et al. |
| 2005/0177227 | A1 | 8/2005 | Heim et al. |
| 2005/0228487 | A1 | 10/2005 | Kujawski |
| 2006/0085080 | A1 | 4/2006 | Bechgaard et al. |
| 2006/0259136 | A1 | 11/2006 | Nguyen et al. |
| 2008/0020977 | A1 | 1/2008 | Lebovitz |
| 2008/0200977 | A1 * | 8/2008 | Paul ...................... A61F 2/2412 623/1.24 |
| 2008/0275540 | A1 | 11/2008 | Wen |
| 2009/0012251 | A1 | 1/2009 | Dirks et al. |
| 2009/0276039 | A1 | 11/2009 | Meretei |
| 2011/0282440 | A1 | 11/2011 | Cao et al. |
| 2012/0053681 | A1 | 3/2012 | Alkhatib et al. |
| 2012/0172978 | A1 | 7/2012 | DuMontelle |
| 2013/0066418 | A1 | 3/2013 | Matheny |
| 2013/0066419 | A1 | 3/2013 | Gregg |
| 2013/0073037 | A1 | 3/2013 | Gregg et al. |
| 2013/0310928 | A1 | 11/2013 | Morriss et al. |
| 2014/0005772 | A1 | 1/2014 | Edelman et al. |
| 2014/0114402 | A1 | 4/2014 | Ahlberg et al. |
| 2014/0135906 | A1 | 5/2014 | Winner et al. |
| 2016/0038280 | A1 | 2/2016 | Morriss et al. |
| 2017/0065408 | A1 | 3/2017 | Grundeman et al. |
| 2017/0065411 | A1 * | 3/2017 | Grundeman .......... A61F 2/2412 |
| 2017/0119523 | A1 * | 5/2017 | Cao ...................... A61L 27/3625 |
| 2017/0156854 | A1 * | 6/2017 | Hammer ............... A61F 2/2412 |
| 2017/0189172 | A1 | 7/2017 | Grundeman et al. |
| 2017/0266000 | A1 * | 9/2017 | Braido ................. A61F 2/2418 |

FOREIGN PATENT DOCUMENTS

| JP | 53-135198 | 11/1978 |
| JP | 2005-527283 | 9/2005 |
| NL | 1008349 | 2/1998 |
| NL | 1008349 | 8/1999 |
| WO | WO 00/62714 | 10/2000 |
| WO | WO 01/28459 | 4/2001 |
| WO | WO 01/41679 | 6/2001 |
| WO | WO 03/024366 | 3/2003 |
| WO | 2004/032987 | 4/2004 |
| WO | WO 2006/050460 | 5/2006 |
| WO | 2010/020660 | 2/2010 |
| WO | WO 2010/020660 | 2/2010 |
| WO | WO 2011/143473 | 11/2011 |
| WO | WO 2012/027487 | 3/2012 |
| WO | WO 2012/047644 | 4/2012 |
| WO | WO 2012/085913 | 6/2012 |
| WO | WO 2012/092437 | 7/2012 |
| WO | WO 2012/110767 | 8/2012 |
| WO | 2012/177942 | 12/2012 |
| WO | 2013/013032 | 1/2013 |
| WO | WO 2013/013021 | 1/2013 |
| WO | WO 2013/103612 | 7/2013 |
| WO | WO 2015/171743 | 11/2015 |

OTHER PUBLICATIONS

International Search Report and Written Opinion of the ISA for PCT/EP2015/059982, dated Jul. 31, 2015, 10 pages.

International Preliminary Report on Patentability for PCT/EP2015/059982, dated Aug. 2, 2016, 14 pages.

JP Application No. 2016-564324, Notice of Reasons for Rejection, dated Mar. 26, 2019.

JP Application No. 2016-564298, Notice of Reasons for Rejection, dated Apr. 2, 2019.

Heim et al, "*Textile Heart Valve: Novel Shaping Process and Material Performances*", Materials and Manufacturing Processes, 26:1303-1309 2011.

Zaidi et al, "*Preliminary experience with porcine intestinal submucosa (CorMatrix) for valve reconstruction in congenital heart disease: Histologic evaluation of explanted valves*", The Journal of Thoracic and Cardiovascular Surgery, vol. 148, No. 5, pp. 2217-2225 (Nov. 2014).

http://www.cs.arizona.edu/patterns/weaving/webdocs/opr_radw.pdf (Oct. 5, 2002).

G. Manoharan, *Prospective, Multicenter Evaluation of the Portico Transcatheter Aortic Valve: Accute Results and 1-year Outcomes*, Cardiovascular Research Foundation, Jun.-Sep. 2012.

N. Dumonteil, *Need for Permanent Pacemaker Following Implantation of the Repositionable Second-Generation LOTUS™ Device for the Transcathether Aortic Valve Replacement: Results from the Reprise II Trial*, Reprise, Oct. 2013.

*Medtronic's CoreValve to Return to German Market*, Qmed Newsletter, Qmed Staff, Nov. 15, 2013.

H.G. Thyregod, *The Nordic Aortic Valve Intervention NOTION) trial comparing transctheter versus surgical valve implantation: study protocol for a randomized controlled trial*, Trials 14, Article No. 11 (2013).

Notices of Opposition (R.79(1) EPC), EP Appln. No. 15723869.2, Aug. 23, 2021.

U.S. Appl. No. 61/989,820, filed May 7, 2014.

Notice of Preliminary Rejection, KR Appln. No. 2016-7030826, dated Aug. 18, 2021 (with English Translation).

Marom et al, "Aortic root numeric model: Annulus diameter prediction of effect post-aortic valve repair," The Journal of Thoracic and Cardiovascular Surgery, vol. 145, No. 2, Feb. 2013, pp. 406-411.e 1.

Medtronic, Nov. 2013, https://www.mddionline.com/medtronics-corevalve-return-german-market.

Abdelghani et al, "A simplified and reproducible method to size the mitral annulus: implications for transcatheter mitral valve replacement," European Heart Journal—Cardiovascular Imaging (2017) 18, 697-706.

* cited by examiner

PROSTHETIC VALVE AND METHOD OF MAKING A PROSTHETIC VALVE

CROSS-REFERENCE SECTION

This application is a continuation of commonly owned copending U.S. Ser. No. 15/857,359, filed Dec. 28, 2017, (now U.S. Pat. No. 10,524,902), which is a continuation of U.S. Ser. No. 15/308,981 filed Nov. 4, 2016 (now U.S. Pat. No. 10,039,640), which is the national phase application of International Application No. PCT/EP2015/059982 filed May 6, 2015, which designated the U.S. and claims priority to EP Patent Application Nos. 14167271.7 filed May 6, 2014, 14167270.9 filed May 6, 2014, 14167269.1 filed May 6, 2014, and 14167272.5 filed May 6, 2014, the entire contents of each of which are hereby incorporated by reference.

GENERAL FIELD OF THE INVENTION

The invention relates to implantable medical devices and methods of making such medical devices, like a prosthetic valve and more specifically a two- or three-leaflet prosthetic heart valve.

BACKGROUND

A typical natural valve of a mammal is the aortic valve, one of the four heart valves. The aortic valve comprises three leaflets, also called cusps, attached to the aortic root that serves as a supporting element for these leaflets. Each of the three leaflets of the aortic valve has a free margin and a margin where it is attached in semilunar fashion to the aortic root. When the valve opens, the leaflets fall back into their sinuses without the potential of occluding any coronary orifice. The hingelines of adjacent leaflets meet at the level of the sinutubular junction, forming at least part of the commissures. The body of a leaflet is pliable, extendable and thin to provide the required flexibility, although its thickness is not uniform. The leaflet is slightly thicker towards its free margin. On its ventricular surface is the zone of apposition, known as the lunule, occupying the full width along the free margin and spanning approximately one-third of the depth of the leaflet. This is where the leaflet meets the adjacent leaflets during valvular closure. With the valve in closed position, the margins of the lunules coapt or meet together, separating blood in the left ventricular cavity of the heart from blood in the aorta. For a valve of this type, or a corresponding type, highest mechanical stresses during opening and closing occur at the commissures and, to a lesser extent, at the free margin of the leaflets.

Prosthetic valves are implanted in the human or animal body and may for instance be used as a passive, one direction prosthetic valve within or nearby blood vessels. They can be completely preformed and implanted as such, or formed in situ using the artificial and/or natural parts needed to form a functional prosthetic valve. A suitable prosthetic valve needs to open and close readily in response to differential pressure on either side of the valve, cause no or only little non-physiological turbulence in the blood flow, and avoid too much regurgitation. Cardiovascular products, such as heart valve prostheses, are thus subject to high requirements with respect to loading conditions, both in magnitude as in number of cycles. Typically, heart valve leaflets may undergo over a billion load cycles in their lifetime. Durability of prosthetic valves, especially of moving leaflets, is therefore an important requirement.

Any prosthetic valve should be able to resist the actual mechanical load on the commissures and leaflet free margin during valvular operation and preferably, maintain to resist such cyclical load during many years. For this, not only initial strength is an important parameter but also reducing the chances of (non-apparent) production anomalies in making the valve.

Today, valves used in valve surgery typically are bioprosthetic valves having leaflets made from biological tissue, often chemically treated bovine pericardium. This is an elastic material that performs relatively well and is able to mimic the natural valve. However, early failure is often encountered, and is believed to be associated with high stresses on the leaflet material upon continuous stretching and retracting under pulsatile load. Various synthetic materials and designs have been proposed as alternatives for making leaflets of prosthetic valves.

A valve prosthesis made using synthetic fibers is for example described in NL1008349. This valve comprises a supporting element carrying a number of leaflets, which have been made by winding reinforcing fibers onto a mandrel in specific directions corresponding to the occurring stresses in the leaflets. Since the fibers have to be positioned according to the maximum stress lines, this valve prosthesis is difficult to make and uses many wound layers to accommodate stresses, whereby mass is added and flexibility may be compromised.

Similarly, U.S. Pat. No. 6,726,715 describes a leaflet for a heart valve comprising a flexible sheet having stress-relieving fibrous elements aligned with predetermined stress lines in the leaflet during valve operation. Sheet material is typically PTFE or PVF, with high-strength/high-modulus fibers as reinforcing elements. Fibers such as carbon, aramid, or polyethylene fibers like Dyneema® UHMWPE fibers may be used.

WO2010/020660 describes making a prosthetic valve from for example a uniform hollow braid made from polyolefin fibers. The hollow braid is shaped to form a valve by pulling it over a mould, comprising a tubular part and a star-shaped part. By subsequently applying heat and pressure, the hollow braid takes the shape of the mould and different sections are created. Around the tubular part of the mould the braid forms into a section that corresponds to a supporting element of the valve, whereas a star shaped part of the mould provides a section that corresponds to multiple valve leaflets. Before removing the valve from the mould, the front and back sides of the valve prosthesis are edge trimmed. To prevent disruption of the trimmed edge, the edge may be heat treated to melt fuse the yarns to each other, provided with a stitching, or otherwise treated to make the edge mechanically stable.

Heim et al. in *Materials and Manufacturing Processes*, 26: 1303-1309, 2011 disclose a method wherein artificial leaflets are made from woven polyester yarns by thermally shaping the woven textile on a mould into a three-cusp geometry; showing that woven polyester could be suited to form a valve prosthesis. Polyester yarn has stretching properties such that the woven textile is able to mimic the natural elastic stretching of a human valve (about 15% of elongation), due to its typical elongation at break of about 14-17%. In order to obtain a valve with good contact between leaflets in closed position and to limit stresses during working cycles, the authors teach to shape the leaflets such that there is a fairly large inherent opening in the centre of the valve, whereas under cardiac pulsatile load adequate coaptation is created over the length of the free margin of the leaflets to prevent or at least minimize regurgitation.

In US2008/0200977 an implantable valve prosthesis is described that includes a frame and at least one leaflet made from a synthetic biocompatible polymer. The leaflet is designed such that its motion aids in preventing blood stagnating in valve pockets, i.e. to prevent thrombus formation. A leaflet is typically formed by casting a solution of polymer, preferably segmented polyurethane, and by then providing two slits to define a free portion that can unrestrictedly move in response to fluid flow to open and closed positions.

A prosthetic heart valve comprising a valve body with multiple leaflets is disclosed in US2003/0114924, which is formed as a one piece by moulding silicone or polyurethane. The valve is moulded to include a gap between the free margins of the leaflets in neutral position, and with leaflets having specific curvature along the free margin; such that under load of fluid flow the gap is closed and leaflet faces engage and form a coaptation area.

US2009/027039 describes an implantable prosthetic valve having at least one leaflet and a restraining member for temporarily preventing substantial movement of the leaflet from open to closed position. A leaflet may be made from various materials, like biological material or synthetic polymers, but is preferably a thin metal film.

In US2005/0137681 a venous valve with a tubular frame and a cover is disclosed, which cover includes surfaces defining a reversibly sealable opening and thus acting as leaflets. The leaflets can have various sizes and shapes, including arcuate edges, curved surfaces, a concave structure, or include a curved support structure to efficiently close the valve and restrict retrograde fluid flow. Leaflets may be made of biologic or synthetic fluid-impermeable material, including ePTFE, PET, urethane and polyethylene.

WO2000/62714 discloses a heart valve prosthesis including a one-piece moulded body with a plurality of leaflets, made from a silicone or polyurethane. In the neutral or rest position, the leaflets' free margins converge to form a non-uniform gap therebetween. The leaflets have a scallop in their free margins, proving sufficient material at the center to seal against reversed fluid flow with minimum coaptation.

U.S. Pat. No. 4,191,218 discloses fabrics for use in vascular prostheses and heart valves, which fabrics are woven from multi-filament (polyester) yarns comprising filaments of about 10 µm diameter, and are heat shrunk to result in open interstitial space of 20-40 µm and elongation in at least one direction of at least 10%. The fabrics preferably have a woven selvedge, which forms the free margin of a heart valve leaflet.

US2012/0172978 describes a prosthetic valve comprising leaflets made from a filter screen material that has uniform pores of 15-60 µm and 10-100 µm thickness, and is woven from e.g. polyester or polypropylene monofilaments. In response to a closed flow pressure the leaflets can be pushed together to engage at the outflow edge, resulting in a coaptation of 3-9 mm. Methods of making such valve comprise forming separately leaflets from the screen material, coupling them together along an attachment line, and optionally coupling to a sewing ring or frame/stent.

In US2005/177227 a method of making a cardiac valve prosthesis is disclosed, wherein a textile membrane, preferably made from polyester or PTFE, is shaped to form leaflets; for example by cutting out segments and using a shaped member reproducing the geometry of a cardiac valve in closed artery position followed by thermofixation.

SUMMARY

The invention relates to a prosthetic valve (400) comprising a leaflet assembly having at least one leaflet (3) attached to a supporting element (2), which leaflet has a free margin (5) that can move between a first position wherein the free margin is flexed away from a closure surface (700) to allow body fluid to flow through the valve, and a second position wherein the free margin abuts the closure surface to close the valve, wherein the leaflet, without pulsatile load on the valve, can form a coaptation height of more than 0.1 mm along the length of the free margin.

The invention is at least partly based on the recognition that known prosthetic valves made from flexible sheet material, as in case of a natural valve, depend on substantial elongation (stretching) of the sheet material from which the leaflet is made, in order to provide sufficient coaptation, that is contacting of the leaflet along its free margin with the closure surface to close the valve, as well as to properly open the valve during closing and opening cycles. Typically elongation has to be up to about 15% in order to provide sufficient coaptation, in particular in the centre of the leaflet (which for a symmetrical cylindrical 3-leaflet configuration coincides with the centre of the valve). This in its turn means that the sheet material has to fulfil stringent mechanical property requirements in order to be able and durably mimic the natural leaflet. Applicant realised that extensive stretching and durability, in particular in a natural environment, which is immunogenic and may give rise to vegetation and other abnormal processes, are hard to combine. Based on this recognition, applicant devised a prosthetic valve wherein also in neutral position, without pulsatile load on the valve, the leaflet is able to abut a closure surface in the valve over a certain minimum coaptation height along its free margin. This coaptation height is contrary to prior art wherein coaptation is generally only created during actual pulsatile load on the valve and thus depends on elongating the leaflet material and the dynamics of the process, rather than creating a valve that meets certain spatial restrictions per se. All-in-all, this means that the material from which the leaflet is made has to meet less stringent demands on extendibility and thus, the current prosthetic valve and methods of making it may provide at least more freedom in sheet material use, and provides the option to make a more durable prosthetic valve. A further advantage includes the possibility to use textile structures made from high-strength, low-elongation biocompatible fibers, and thus use of thin flexible fabrics, preferably woven fabrics, for making prosthetic valves.

It is noted that the invention does not exclude that upon coaptation at some point along the free margin, small channels or other openings can temporarily be present for example due to the dynamics of the pulsatile process. The formation of wrinkles or other temporary imperfections in the sheet material does not preclude the valve from proper functioning, as long as the leaflet has a geometry that intrinsically allows to close the valve along the length of the free margin without pulsatile load, that is without requiring extension of the leaflet. Stated otherwise, the one or more leaflets have such geometry that without pulsatile load a certain minimum coaptation area is possible, such area defined by the coaptation height and the length of free margin of a leaflet abutting the closure surface, thus preventing significant regurgitation in the valve during actual use. Such geometry also results in sufficient coaptation and effective valve closing with pulsatile load during use, even if the free margin itself would locally not fully abut the closure surface.

The invention also relates to a leaflet assembly for use in a prosthetic valve, as further described herein. The invention further concerns methods of making the prosthetic valve, including making the leaflet assembly. More specifically the invention concerns a method of making a prosthetic valve comprising a at least one leaflet attached to a supporting element, which leaflet has a free margin that can move between a first position wherein the free margin is flexed away from a closure surface of the valve to allow a body fluid to flow through the valve, and a second position wherein the free margin abuts the closure surface to close the valve, the method comprising providing a sheet material, and forming a leaflet assembly comprising at least one leaflet and a supporting element from the sheet material, wherein forming the leaflet assembly comprises shaping the leaflet to impose a geometry wherein the leaflet, without pulsatile load on the valve, can form a coaptation height of more than 0.1 mm along the length of the free margin.

It is noted that "forming a leaflet assembly from the sheet material" may include steps such as folding, cutting, shaping the leaflet in a mould, assembling multiple pieces of sheet material, connecting by stitching, gluing, etc. . . .

Definitions

A prosthetic valve is a constitution of at least one leaflet and supporting element, wherein the leaflet is attached to the supporting element such that the leaflet can flex or hinge to provide an open as well as a closed position for the valve, and may optionally comprise a rigid or semi-rigid support, also called frame or stent.

A leaflet assembly is the combination of at least one leaflet and corresponding supporting element in a generally tubular configuration, and may be made from multiple pieces of material connected together or from one single textile structure (like a woven fabric). The leaflet is the movable part and is attached to the supporting element, also called graft or skirt, and together they define pockets that can be filled with fluid to close the valve.

A commissure is generally a point or line along which two things are joined; in anatomy of natural heart valves a commissure is the distinct area of junction between two adjacent valve leaflets and their supporting vessel wall. Within the present application the commissure refers to the attachment line or region from the outflow side between a leaflet and supporting element in case of a stent-less valve, and between leaflet and stent, and optionally supporting element for a stented valve. In addition to connections forming a commissure, there can be further connections between leaflet, supporting element and/or stent, for example further defining leaflet shape.

A margin of a leaflet is an edge.

Coaptation means abutting, contacting or meeting of a leaflet and a closure surface, such as another leaflet, to close the valve; coaptation height refers to the height or length of coaptation measured from the free margin in longitudinal direction of the valve, i.e. towards the bottom of the leaflet.

The centre line of a leaflet is a hypothetical line from the free margin at the centre of the valve to the nadir at the bottom of the leaflet, that is the lowest point defining the leaflet by connections to the supporting element. In case of a non-symmetrical valve with for example three leaflets, it is the line from the contacting or coaptation point of the three free margins to the nadir.

The curvature height characterizes the curvature in the leaflet of a valve as the largest orthogonal distance between the centre line and a straight line connecting the free margin at the centre of the valve and the nadir.

The radius of curvature of a leaflet is the radius of a circle that best fits a normal section of the curved surface of the leaflet in closed valve position.

An elastic material is a material that is capable of returning to its original shape after being deformed.

To impose a geometry on an object means that the geometry of this object is established by the creation of the object, as opposed to a geometry that can arise due to external forces applied to the object after creation.

Inflow side or bottom side of the valve means the side where fluid enters the valve when it is in open position, the opposite side is referred to as outflow side or top of the valve.

For something to run parallel with another thing means that both things predominantly extend in the same direction.

The elongation at break of a specimen is the elongation of that specimen recorded at the moment of rupture thereof under an applied load, expressed as a percentage of its original length. For sheet material, the elongation at break is often also called elongation at rupture or elongation at fracture.

A yarn is an elongated body having a length much greater than the width of its cross-section, typically comprising a plurality of continuous and/or discontinuous filaments, said filaments being preferably aligned substantially parallel to each other.

Adjacent means adjoining or nearest in position.

A selvedge (or selvage) is an edge of a woven structure wherein the threads that run in a direction perpendicular to the edge of the structure are not extending from the structure as free ends, but are continuous at the edge by returning into the structure. Selvedges are typically formed in fill (also called weft) threads during a shuttle weaving process, but may also be made with other techniques or in warp threads.

DETAILED DESCRIPTION

Figure 1A:
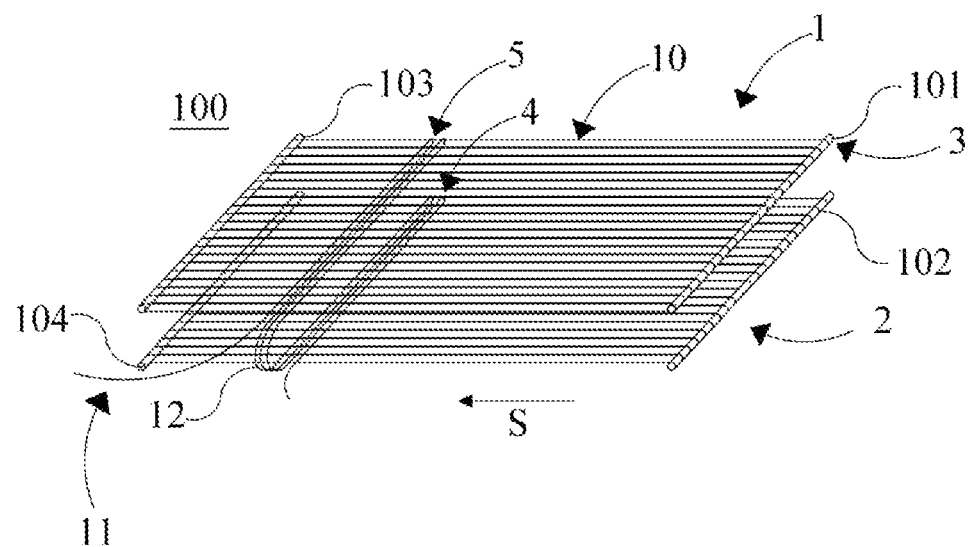
FIGS. 1A-1I schematically show various steps for forming a valve prosthesis using a method according to the invention.

In a first embodiment the at least one leaflet of the prosthetic valve is formed to have such imposed geometry that—without pulsatile load—coaptation with a coaptation height of between 1 and 15 mm is possible. It was found that such a height creates an adequate coaptation area that effectively prevents regurgitation upon reversed fluid flow, while allowing fast and complete opening for fluid passage. Preferably the leaflet geometry is made such that the coaptation height is at least 2, 3, 4 or 5 mm and at most 15, 13, 11, 10, 9, 8, or 7 mm, for example between 3 and 10 mm, preferably between 5 and 7 mm.

In another embodiment the geometry imposed to the leaflet comprises a convex surface, relative to fluid entering at the bottom of the valve, having a radius of curvature at the centre line of the leaflet of between 1 and 20 mm, for example 1, 2, 3, 4, 5, 6, 7, 8, 9, 10, 11, 12, 13, 14, 15, 16, 17, 18, 19 or 20 mm, preferably about 12 mm. It is believed that an imposed convex geometry with this particular small radius, as opposed to typical radii in known prosthetic valves of 50 mm or above, leads to less stress and deformation in the leaflet material and possibly less tension on the commissures. Such geometry also results in pockets defined by leaflet and supporting element with relatively large volume, which will be filled with fluid during closing. This may be advantageous for effective re-emptying upon opening, preventing e.g. blood remaining in a pocket and reducing risk of thrombus formation.

In still another embodiment the imposed geometry of the leaflet comprises a curved convex surface, wherein the curvature height of this curved surface at the centre line of the leaflet is more than 1 mm, preferably more than 2, 3 or 4 mm most preferably about 5 mm. A maximum value is inherently dependent on the outer dimensions of the valve itself, but is typically about 10-15 mm, for example 10, 11, 12, 13, 14, or 15 mm. It is believed that an imposed convex geometry with this particular shape, as opposed to typical heights between 0 and 1 mm for prior art valves, leads to less stress in the leaflet material and possibly less tension on the commissures. It is noted that the curvature of leaflet surface may be dependent on diameter of a valve, i.e. a larger diameter valve may have a correspondingly larger curvature.

In yet another embodiment the leaflet is formed such that the free margin of the leaflet has excess length relative to the theoretical length needed for closing the valve; for example relative to the distance between the two ends of the free margin at the commissures via the centre of the valve in case of a substantially cylindrical valve with at least two leaflets. In order to create a preferred coaptation height of at least 1 or at least 3 mm along the length of the free margin of the leaflet, applicant found (contrary to the common design of pericardium material like Carpentier-Edwards PERIMOUNT or textile designs like the design of Frederic Heim as described here above) that it is advantageous to create excess free margin length. Such excess length can be made in different ways. For example, in case of a substantially cylindrical valve with radius R, and having three leaflets of same size that are attached to the supporting element with even distribution between commissures the needed theoretical free margin length would be 2 R. By making leaflets having at least the same size as the supporting elements their free margin length would be at least 2 πR/3; thus creating an oversize factor of at least about 1.05. Still more oversize can be obtained by designing leaflets and optionally supporting elements to be larger relative to actual size of the valve or its stent during use. This can for example be done by reducing the diameter of a prosthetic valve comprising a stent and a leaflet assembly of matching diameters by compressing the stent. It is noted that US2005/177227 describes a cylindrical valve with 3 leaflets, and indicates the length of the free margin of a leaflet to correspond to twice the length of the radius R, and thus to be less than the corresponding segment at the periphery of 2 πR/3, in order to guarantee closure of the valve during diastolic phase. In general it was found to be advantageous to make a valve wherein the leaflet free margins have a total oversize or excess length factor of at least 1.07, preferably at least 1.09, 1.11, 1.13 or 1.15, and preferably of at most about 1.4, more preferably at most 1.3, relative to the theoretical length needed for closing the valve (for example relative to the minimum length needed to bridge the distance between commissures via the center of the valve). Stated otherwise, the free margins preferably have an excess length of at least 7%, more preferably of at least 10 or 15%, and of at most 40 or 30%.

In a further embodiment the excess length of a leaflet is created by one or more of the method steps chosen from the group of preforming the sheet material to a specific shape, for example by forming a trapezium-like sheet material (i.e. a form wherein a section that corresponds to the leaflet forms the wider bottom half of the trapezium and a section that corresponds to the supporting element forms the smaller upper section of the sheet material), or forming a tapered or conical tubular material, reducing the outer circumference of the valve, for example by using a retaining ring or compressing a stented valve, and shifting the leaflet surface before final fixing of the leaflet in the valve.

In still another embodiment a valve is made wherein the leaflet is attached to the supporting element along a commissure, which runs at least for a certain length starting at the free margin in parallel with the body fluid flow, that is parallel to the longitudinal axis of the valve. This way the stress on the commissure is not concentrated at one point at the top edge, as in common designs, but is divided over said length, which may increase durability. In case the valve comprises a rigid support or stent, the stent preferably has vertical posts to which the leaflet assembly is connected as part of forming a commissure, resulting in a stable and durable commissure. The commissure can run over the height of leaflet assembly or stent, but preferably has a length of 1-9 mm from the outflow side, or of 1-6 mm. It will be clear that commissure length may be proportional to size (height) of the valve.

In again another embodiment wherein the sheet material is an elastic material, the sheet material has an elongation at break of 10% or less. It is an advantage of the present method, and completely against the teaching of prior art to use a material that allows elastic stretching of about 15% or more (mimicking the stretch behaviour of natural leaflet material), that also a low-stretch sheet material, i.e. material that can be substantially less stretched and has substantially lower elongation at break, can be used for forming a leaflet of a valve prosthesis. Less stretching during use is believed to provide more durable leaflets and valves after implantation, not only from a mechanical point of view but also since stretching an object may induce collagen growing over this object. The low stretch characteristics of present leaflets thus reduce or even minimize the impetus of potential collagen or connected tissue overgrowth, that would otherwise result in leaflet thickening and loss of mobility and possibly induce focal thrombi or other vegetation. In general, tissue overgrowth or fibrosis may lead to leaflet compaction, which will result in valvular incompetence. Preferably the elongation of the sheet material during its use in the valve made according to the invention is less than 9, 8, 7, 6, 5, 4, 3, 2 or even 1%. The elongation at break of such sheet material, occurring at higher load than during use as leaflet, is similarly less than 9, 8, 7, 6, 5, 4, 3, 2 or even 1%. Without wishing to be bound to any theory, it is thought that imposing a leaflet geometry that also without load can provide a certain minimum coaptation height, apparently allows a sheet material to be used that is low in stretch or has a high mechanical resistance to stretching; that is a sheet material with a high tensile modulus (also called Young's modulus).

Although for example porcine intestinal submucosa (Cor-Matrix™) is a natural elastic sheet material that can be used for creating leaflets in a valve prosthesis (see for example Zaidi et al., doi: 10.1016/j.jtcvs.2014.02.081), in an embodiment the sheet material is a textile structure comprising one or more elastic yarns having an elongation at break of 10% or less. As shown in some of the above cited patent publications, a textile structure may also be suitable for making a leaflet. Textile materials are easy to produce industrially on a large and controllable scale. By using yarns that have an elongation at break of less than 10%, preferably less than 9, 8, 7, 6 or 5%, preferably between 1 and 5%, the low stretch advantages as described here above can be easily obtained. Textile structures or fabrics may be made with techniques like knitting, braiding, or weaving.

In a further embodiment the textile structure is a woven fabric made from one or more threads or yarns. A woven structure has the advantage over for example a knitted or braided structure in that desired (non- or low-) stretch properties and shape or form can be easily incorporated by applying various weaving techniques, and by using various yarns as warp and fill (or weft) threads. Weaving pattern is not found to be particularly critical, the skilled person will be able to select a pattern in combination with selected threads to obtain desired properties with some experiments. Typically, woven fabrics with commonly used patterns like plain, twill or basket weave patterns are found to provide good performance.

One or more textile structures can be applied as sheet material for forming leaflets and a leaflet assembly. Suitable methods include forming each leaflet and supporting element from a separate piece of sheet material or textile structure and then connecting the various pieces together; forming multiple leaflets from one textile structure and multiple supporting elements from a separate textile structure and then connecting the two parts together; and forming multiple leaflets and supporting elements from a single textile structure into a leaflet assembly. For example, a leaflet assembly having three leaflets and supporting elements may thus be made from 6, 4, 2, or 1 piece(s) of textile, preferably woven fabric. Suitable methods for forming a leaflet assembly from a single woven fabric include applying double weaving techniques that result in multilayer woven fabric, like a so-called double width fabric that is open at one side, or a flattened tubular fabric; as will be further described below.

In a further embodiment the free margin of the leaflet is woven as a selvedge. A woven selvedge or simply selvedge (selvage in US English) is a self-finished edge of a woven textile structure. A selvedge refrains the textile structure from unraveling or fraying, but, as opposed to other types of stabilised or finished edges, a selvedge is the result of the actual weaving process, and not of an additional process step such as cutting, melting, stitching or other process for providing a stabilised edge. In a woven textile structure, selvedges typically (but not necessarily) run parallel to the warp threads and are formed by the fill thread(s) looping back into the fabric around the last warp thread after exiting. A selvedge is made inherently if fill threads are supplied endlessly as in a shuttle weaving process, but can also be made in a shuttle-less weaving operation by tucking-in the fringed ends of the fill threads after each interlacing and cutting. A further method is introducing additional threads with so-called leno selvedge design that lock outermost thread ends at the edge of the fabric. By having the free-margin woven as a selvedge, this free margin is provided as an inherently mechanically stable edge without using an additional process step such as melting or stitching. Additional process steps may complicate the manufacturing process of the valve as a whole, and also may give rise to side effects, like alteration of mechanical properties of the yarns (such as for example increased stiffness, reduced resistance to wear or reduced strength) upon melt fusing of loose yarn ends, or local thickening and reduced flexibility of the fabric after edge stitching. Nevertheless, such additional edge finishing may be suitably used to stabilise edges of a woven fabric for use in making a prosthetic valve; for example in case of making a continuous or endless woven fabric that later is to be cut into desired lengths for forming e.g. leaflets. A suitable example of making a stabilised or finished edge is hot cutting of woven fabric, e.g. with a laser or with an electronic thermal cutter, also called hot knife, which allows simultaneously cutting and fusing fabrics of thermoplastic fibers in a controlled single step. Alternatively, threads with leno design may be included during weaving of the fabric at the places where the fabric is to be cut.

In particular it has been found that it is advantageous to weave the textile structure as a multilayer structure comprising stacked layers, which layers are preferably interconnected by crossing of warp or fill threads at desired locations, or alternatively interconnected by sewing or stitching after weaving. Applicant recognized that by applying a weaving process wherein a woven textile structure is made that comprises multiple stacked layers—such process is commonly referred to as a "double weave" process and is typically used for making decorative fabrics-supporting element(s) and leaflet(s) can be formed in one weaving process in the same textile structure, namely as different layers (or as sections in different layers) of such textile structure. At the same time leaflet and supporting element may attain a mutual configuration in the structure or subsequent leaflet assembly that corresponds to the mutual configuration the leaflet and supporting element need to have in the ultimate valve, and also commissures may—at least partly—be obtained as a direct result of the weaving process. In such multiple layer weaving, the longitudinal sides of layers can be made as open edges, typically with a selvedge, or can be closed edges, by connecting two layers at their edges. Considering the size of a valve for use in a bodily conduit like blood vessels or arteries, the width of a textile structure for making a leaflet assembly will be on the order of centimetres. Such size may appear relatively small for (industrial) woven fabric production, but suitable weaving methods, weaving patterns and machinery are known in the art for such purpose; for example those generally referred to as narrow fabric weaving (systems) that are typically used for making tapes and ribbons. In such weaving equipment, typically movement of every warp thread can be individually controlled to make multiple layers, and various connections between layers. Further information on such weavings methods is available on the internet, for example on double weaving in the document available via http://www.cs.arizona.edu/patterns/weaving/webdocs/opr_rgdw.pdf.

In an embodiment a leaflet assembly is made from a single piece of a flat woven fabric, by folding to itself, forming into a tubular configuration by connecting the ends, and making further connections between the two layers to define leaflets and supporting elements.

In another embodiment a single woven textile structure is made by a double weaving process resulting in a two-layer woven fabric, for example a so-called double width fabric that has two selvedges at its open side, and a continuous fold line at the opposite closed side. In such structure one layer will form supporting elements and the other layer leaflets. The width of a layer is determined, for example, by the number of warp threads and warp thread dimension, and both layers can be made to have the same or different width or size by varying the respective number of warp threads in each layer. In such weaving process, further connections can be made between the layers by crossing warp and/or fill threads from one layer to another; this way for example at least partly defining a leaflet by a connecting line (which can be a commissure). The spatial arrangement of connecting lines will define the form and size of the leaflet and its free margin, and of the corresponding supporting element. The leaflet can be made to have a larger size than the corresponding supporting element—to create excess length of the free margin in the final valve—by (locally) increasing the number of fill threads in (the layer forming) the leaflet relative to its supporting element.

A woven fabric, including a double width fabric as described above, can be made as a fabric of distinct length in a discontinuous process, as on a classical loom with warp threads attached to beams, but also in a continuous weaving operation by continuously feeding warp threads to the warp beam. In the latter case a continuous (or endless) fabric results, which can be cut into desired lengths. In both cases the obtained piece of fabric can be made into a tubular structure by connecting the fabric edges with warp (or cut) ends together. A two layer woven fabric then results in a tubular structure, wherein supporting elements will form the outside and leaflets are on the inside of the structure. The warp threads in these embodiments run parallel to the free margin, which is a selvedge of the fabric (similarly for top edge of supporting elements).

In another embodiment, a woven textile structure is made by a double weaving process that results in a seamless tubular fabric, also called flattened tubular fabric, flat-woven tubular fabric or hollow elongate fabric; as it results from a continuous fill thread crossing over from one set of warp threads forming a first layer to the other set forming another layer at each side edge after every interlacing. It is noted that in such case an uneven total number of warp threads is used to omit weaving errors, typically referred to as 'error corrected tubular weaving' in the art.

In an alternative embodiment, a tubular woven fabric is made by using an endless warp beam, like a circular or triangular beam. Further, in addition to a one tube or one channel structure, also multi-channel or multi-layer tubular woven fabrics can be made by using multiple sets of warp threads and beams, specific designs of endless beams (that is beams having ends joined, like a circular loop), and/or specific crossing patterns of threads between the layers or tubular structures.

As also described above, tubular fabrics can be made in a continuous weaving process or in a dis-continuous weaving operation. In an embodiment of the invention the method comprises continuous weaving, and the resulting endless (multi-) tubular woven structure is subsequently cut into desired lengths. One of the cut ends of the tube will form the free margins of leaflets, but since warp threads running lengthwise in the tube will after cutting extend from the fabric edge, a finishing step to stabilize the cut end is applied. Various finishing methods can be used for both ends of the tubular structure, preferably a thermal treatment is applied to a woven fabric made from thermoplastic polymer fibers. More preferably cutting and finishing is combined by using a hot knife or other thermal cutting method. After finishing the cut edges, the tube may be partly inverted; i.e. part of the tube will form a tube within the tube and by making connections between the tubes the outside will form supporting elements and inside one or more valve leaflets.

In another embodiment a tubular woven fabric is made piece-by-piece by a dis-continuous weaving process. This has the advantage that a selvedge can be woven in the warp threads, by not connecting the warp threads directly to the warp beam but via additional threads and/or hooks; for example using the Pueblo-Navajo or warp selvedge system as known in the art.

In an exemplary embodiment a substantially cylindrical tube is made, ends are optionally stabilised, and subsequently the tube is partly inverted to make a tube within the tube. The free margins of the leaflets will in this case be of substantially the same length as the corresponding supporting elements; this way having an excess length of about 5%. In a further embodiment a tapered tube is made, preferably by using a weaving process including gradual changes in number of warp threads in the woven fabric as described in U.S. Pat. No. 5,800,514 or US2014/0135906. A length of tubular fabric having a first diameter at one end that is larger, preferably at least 2 or 5% larger, than the second diameter at the opposite end and with a gradual transfer of first to second diameter is provided, the ends are optionally stabilized. Then the tube is partly inverted such that the inner tube has a larger diameter than the outer tube; meaning the free margins of the leaflets will have an excess length of more than 5%. Multilayer tubular structures, as described further using drawings hereafter, can be processed in similar ways to form a leaflet assembly for use in the method of the invention.

Preferably, a textile structure comprising one or more elastic yarns having an elongation at break of 10% or less is used as sheet material for making a leaflet assembly. In a further embodiment the elastic yarn has a linear density of less than 120 dtex, preferably a linear density of less than 100, 80, 60, 50, 40, 30, 20 or even 15 dtex, preferably linear density of at least 5, 7, or 10 dtex; for example a linear density of between 5 and 30 dtex, or between 7 and 15 dtex. Applicant found that there may be a major advantage in applying textile structures made from thin yarns for making a prosthetic valve (note: although dtex is not a parameter that denotes actual dimension or spatial length, in practice it corresponds to yarn diameter since most synthetic and natural materials for making yarns have a density of about 1 kg/dm$^3$). Particularly, it was found that using such thin yarns in the textile structure leads to a fabric that is very flexible, and thus enabling fast response of the leaflet under pulsatile load. The flexible leaflets can also easily align with the supporting elements, thus creating a large effective orifice; and also induce less load on the commissure. Furthermore, it was found that the use of such thin yarns tends to lead to textile structures having relatively low pore size and low permeability, in particular in case of a woven structure. Combined with above mentioned reduced risk of thrombus formation, this may contribute to good biocompatibility, high effectiveness, as well as durability of the valve.

Similarly, it was found to be advantageous that the thickness of single layers of the textile structure, preferably a woven fabric, is preferably at most 200, 150, 120 or 100 µm and at least 20, 30, 40 or 50 µm for optimal performance, for example between 40 to 150 µm, preferably a thickness of between 50 to 100 µm. In case of woven fabric, this layer thickness typically corresponds to a plain weave, basket weave or twill weave of (UHMWPE) filaments in warp and fill direction having a linear density of between 5 to 50 dtex.

In yet a further embodiment the textile structure comprises high-performance polymeric filaments, preferably having high tensile strength or tenacity of at least 1 GPa and high tensile modulus of at least 30 GPa. Examples include carbon fibers, aromatic polyamide fibers, aromatic polyester fibers, and ultra-high molecular weight polyolefin fibers. Preferably the textile structure comprises ultra-high molecular weight polyethylene (UHMWPE) fibers, more preferably the textile structure comprises at least 80 mass % of UHMWPE filaments with a tenacity of at least 2 GPa, more preferably the warp and/or the fill threads substantially consist of UHMWPE filaments. Such multifilament yarns have been found to be ideally suitable for use in woven fabric for making leaflets and supporting elements of a valve prosthesis. The UHMWPE yarns are durable, can be made with the desired mechanical properties and a medical grade is available commercially, which medical grade is hardly immunogenic. In particular, it is preferred to use UHMWPE yarn that has an intrinsic viscosity (IV) of at least 5 dl/g, preferably at least 10 dl/g, more preferably at least 15 dl/g. Preferably, the IV is at most 40 dl/g, more preferably at most 30 dl/g, even more preferably at most 25 or 20 dl/g. IV is determined according to method PTC-179 (Hercules Inc. Rev. Apr. 29, 1982) at 135° C. in decalin, the dissolution time being 16 hours, with DBPC as anti-oxidant in an amount of 2 g/l solution, by extrapolating the viscosity as measured at different concentrations to zero concentration. Particularly preferred are gel-spun UHMWPE yarns, which typically have a Young's modulus of at least 30 or 50 GPa. Preferably the UHMWPE yarn has a tenacity of at least 1.2 GPa. Preferably the yarn used according to the invention comprises at least 90 wt-% UHMWPE filaments and most preferably the yarn used according to the invention consists of UHMWPE filaments, and has a Young's modulus of at least 50 GPa. A preferred example of an UHMWPE yarn is Dyneema Purity® yarn obtainable from DSM, The Netherlands. This type of UHMWPE yarn is particularly preferred, being medical grade yarn available in low dtex versions, the yarns typically having an elongation at break of around 2 to 4%. Tensile strength (or strength) and tensile modulus (or modulus) of UHMWPE yarn are defined and determined at room temperature, i.e., about 20° C., on multifilament yarn as specified in ASTM D885M, using a nominal gauge length of the fibre of 500 mm, a crosshead speed of 50%/min and Instron 2714 clamps, of type "Fibre Grip D5618C". On the basis of the measured stress-strain curve the modulus is determined as the gradient between 0.3 and 1% strain. For calculation of the modulus and strength, the tensile forces measured are divided by the titre, as determined by weighing 10 metres of yarns; values in GPa are calculated assuming a density of 0.97 g/cm$^3$. The ultra-high molecular weight polyethylene may be linear or branched, although preferably linear polyethylene is used due to the very high tenacity and modulus obtainable by stretching during manufacturing of the yarn. Linear polyethylene is herein understood to mean polyethylene with less than 1 side chain per 100 carbon atoms, and preferably with less than 1 side chain per 300 carbon atoms; a side chain or branch generally containing at least 10 carbon atoms. The number of side chains in a UHMWPE sample is determined by FTIR on a 2 mm thick compression moulded film, by quantifying the absorption at 1375 cm using a calibration curve based on NMR measurements (as in e.g. EP0269151).

In another embodiment, typically in case the sheet material is formed from semi-crystalline thermoplastic polymer, forming a leaflet assembly may further comprise shaping the leaflet by contacting with a mould of desired shape, optionally heating the mould to a temperature of 3-60° C. (preferably 5-40° C.) below the melting point of the sheet material (i.e. the melting point of the polymer from which the sheet is made; see ISO11357-3 for a determination of the melting point of a polymer), optionally creep forming (i.e. altering its dimensions) the sheet material, and submitting it to a controlled relaxation and/or plastic stretching to conform to at least a part of the mould. Such thermal forming process is for example described in WO2010/020660. With this embodiment the geometry of the leaflet can be further fine-tuned, for example to create certain curvature or to meet certain clinical demands.

In yet another embodiment, also typically in a situation wherein the sheet material is formed substantially from a semi-crystalline polymer, the method further comprises steps of decreasing the permeability of the sheet material by applying a coating or optionally arranging the sheet material, preferably a textile structure, in a mould, heating to a temperature of 3-15° C. below the melting point of the polymer, and holding at a temperature of 3-15° C. below the melting point of the polymer for 10 seconds to 2 hours to impart a partial connection between adjacent filaments and/or yarns in the textile. Depending a.o. on the cross section of the yarns and their arrangement in the textile structure (for example type of weave), it can be advantageous to decrease the permeability of the textile structure. In this embodiment the thermo-mechanical properties of the polymers of which the yarns are made can be used to improve the permeability properties of the textile structure.

In a further embodiment, the prosthetic valve further comprises a stent (also called rigid carrying structure or frame) and the method further comprises connecting the at least one leaflet and supporting element to a stent. Connecting may be done by using one or more connecting means, preferably connecting is done by applying stitches. Suitable stitches have such strength properties that a durable connection is obtained under the loading during use as prosthetic valve. Preferably stitches are made by using a yarn or suture material that has similar strength as the yarns in leaflets and supporting elements, more preferably by using the a yarn or a suture of suitable size or linear density, and comprising at least 80 mass % of or made essentially from the same type of yarn as in leaflets and supporting elements.

With regard to the use of a rigid carrying structure or stent, such a stent typically comprises a rigid member, and often is of ring or cylindrical shape. Suitable materials for making a stent include rigid polymers, fiber-reinforced polymers, metals and their alloys, ceramics and combinations thereof. Suitable rigid polymers include polyacetals, dextroplast, polyurethane, polyethylene, polysulfones, polyethersulfones, polyarylsulfones, polyetheretherketones, and polyetherimides. Suitable metals include biocompatible metals, such as, stainless steel, titanium, cobalt alloys, such as Elgiloy®, a cobalt-chromium-nickel alloy, and MP35N, a nickel-cobalt-chromium-molybdenum alloy, and Nitinol®, a nickel-titanium alloy. In addition, stents can be produced from ceramic materials, such as pyrolytic carbon, silicon carbides or metal carbides, hydroxyapatite and alumina. Suitable stents can also be produced from carbons such as graphite. Preferably, a stent is at least partly made from a super elastic alloy, or a shape memory alloy, such as Nitinol®, a nickel-titanium alloy, that is available as a super elastic material, as well as a shape memory alloy. Such a stent allows to easily insert the valve prosthesis into the body in a desired position. Before insertion, the self-expandable stent is brought to a first (relatively low) temperature at which it has a compact configuration. This compact configuration allows to easily insert the stent (and the valve in conjunction therewith) into the body, using minimal invasive surgery. After positioning the stent, and due to the body temperature, the shape memory alloy will heat up and change phase, thereby changing its shape. For Nitinol® for instance, a phase change will occur between an austenitic phase and a martensitic phase. As a result the stent will expand and thereby create a clamping force against surrounding tissue. In another configuration, Nitinol® is super elastic and can be elastically deformed up to material strains of about 10%, thus deformation of a valve towards a compact shape is possible, still allowing elastic deployment to the final shape after placement.

The prosthetic valve made by the present method may be stent-less or may contain a stent attached to the leaflet assembly. A stent-less valve or leaflet assembly may be also used as a valved graft or grafted valve; meaning that the supporting element layer thereof can be attached to the wall of a blood vessel or artery and function as a graft to (partly) replace or reinforce a weak or aneurismal vessel. In such embodiment the outside of the leaflet assembly, the supporting elements layer, may be further treated to reduce permeability, e.g. by providing a coating or a further layer of material. A prosthetic valve with a stent provides some other advantages, for example the possibility of being implanted via minimal invasive techniques using catheter systems. In an embodiment the method thus further comprises attaching the leaflet assembly to a stent.

In another embodiment the prosthetic valve comprises two leaflets as defined herein above, wherein the second leaflet acts as the closure surface for the first leaflet and vice versa. The prosthetic valve may also comprise three leaflets, in which case each leaflet acts as the closure surface for the other two leaflets.

The prosthetic valve as described herein can be used to replace a mammal valve, like a human venous or a cardiac valve, via a surgical treatment; via classic operations or by minimal invasive and percutaneous techniques, depending on the type of stent optionally used in the prosthetic valve.

In addition to the above described embodiments, the prosthetic valve and methods of making such valve will now be further explained using a number of schematic drawings, which are not necessary to scale, and may not show all features or components for clarity reasons. Like reference numbers in different figures refer to like features.

FIGS. 1 1A through 1L schematically show various steps of an embodiment of the method of forming a prosthetic valve. In FIG. 1A a loom 100 is depicted, the loom having four warp beams (or loom bars) 101, 102, 103 and 104. Warp yarns 10 are connected between the top two warp beams 101 and 103, and between the bottom two beams 102 and 104. This way a textile structure having two stacked layers can be formed in one weaving process, using one loom set-up. For reasons of clarity, common other parts of the loom, such as the heald frames (or harnesses) with heddles to separate with a predetermined pattern warp yarns in one layer (or in both layers) to form a clear space (or warp shed) through which (a shuttle or pick carrying) the fill (also called weft) yarn can pass, and the optional bat (or reed) for pushing the fill yarn against the fell of the cloth, are not shown. Warp yarns may be attached to the beams (typical for a dis-continuous process), or may be continuously fed with beams 101 and 102 as guiding members, and 103 and 104 in such case representing a single fabric beam for receiving the two-layer fabric made. The fill yarn 11 as shown in FIG. 1A is woven in the upper layer 3 of the textile structure 1 by interlacing the fill yarn with the upper warp yarns (e.g. forming a plain weave), and passes back at the edge 5 of layer 3 towards fold line 12, where it is woven in the lower layer 2 until it reaches edge 4 of this lower layer and passes back towards fold line 12. Note that for clarity the fold line is made to look larger in the figure than in practice. This way, the edges 5 and 4 are formed as selvedges. The weaving process continues until the textile structure has the desired size. The result is a two layered woven textile structure comprising a first distinct layer 2 having a selvedge 4, and a second distinct layer 3 having a selvedge 5. Layer 2 is connected to layer 3 along the fold line 12, by having fill yarns passing from the one layer to the other. These layers 2 and 3 will form respectively supporting element and leaflets of the ultimate valve, and the fold line 12 may form a part of the connections between supporting element and leaflet. An alternate embodiment further includes interweaving of the layers 2 and 3 by crossing yarns between layers other than at the fold line, to result in further connections and forming e.g. more sections in a layer.

Figure 1B:
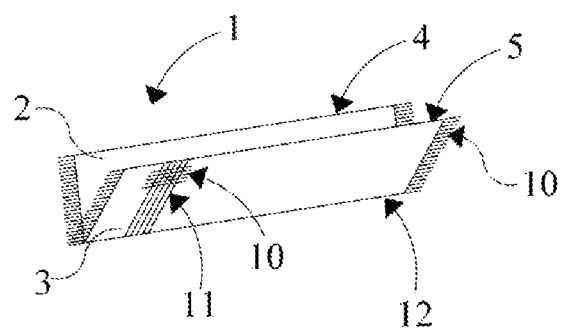

After the textile structure 1 is woven on the loom 100, it is released from the loom as is shown in FIG. 1B. It is now clear that the textile structure is woven as a double weave (or double width) cloth, having distinct layers 2 and 3, each having a selvedge 4 and 5 respectively. The warp yarns 10 extend over a little length outside of the actual textile structure at the non-selvedge edges. These edges may optionally be stabilized, at this stage or later.

Figure 1C:
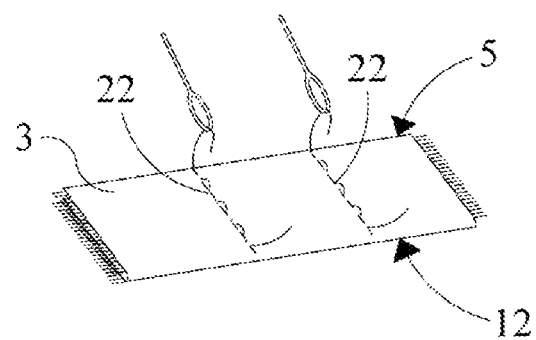

In a next step, as depicted in FIG. 1C, stitches 22 are added further (next to fold line 12) connecting the layers 3 and 2. By adding two lines of stitches 22 to this structure, layer 3 is divided in three separate sections corresponding to separate leaflets in the valve.

Figure 1D:
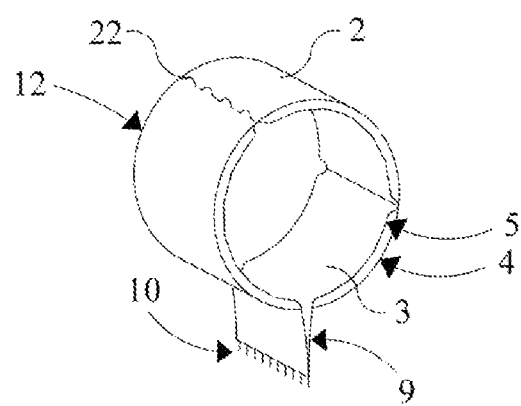
Figure 1E:
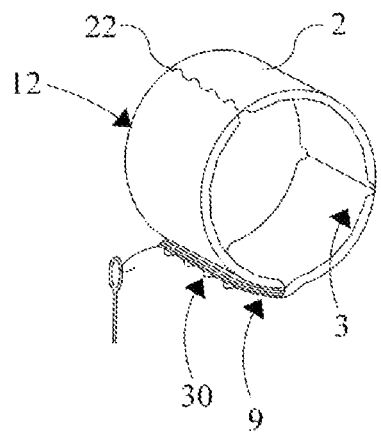

In a next step, as depicted in FIGS. 1D and 1E, the two non-selvedge edges are brought together (i.e. the proximal end and distal end of the structure are configured on top of each other), such that the textile structure forms a tubular structure. As can be seen in FIGS. 1D and 1E, the leaflets of layer 3 are situated on the inside, while the supporting elements of layer 2 are situated on the outside of the structure. At the closure 9 of the loop, the warp yarns 10 of both edges of the textile structure meet. Subsequently, the closure 9 of the loop is processed to make sure the closure can withstand the mechanical forces exerted on the prosthetic valve when in use. Firstly the loose warp ends may be cut and then, as can be seen in FIG. 1E, the closure 9 is folded towards the surface of layer 2 and thereafter secured with stitches 30. Alternatively, the folded ends are first rolled up and thereafter folded against layer 2. This way, any loose warp yarns ends are no longer freely exposed, but a disadvantage is that the rolled up closure 9 is somewhat thicker as compared to a non-rolled up closure. A further alternative is to stabilise the edges before stitching to layer 2.

Figure 1F:
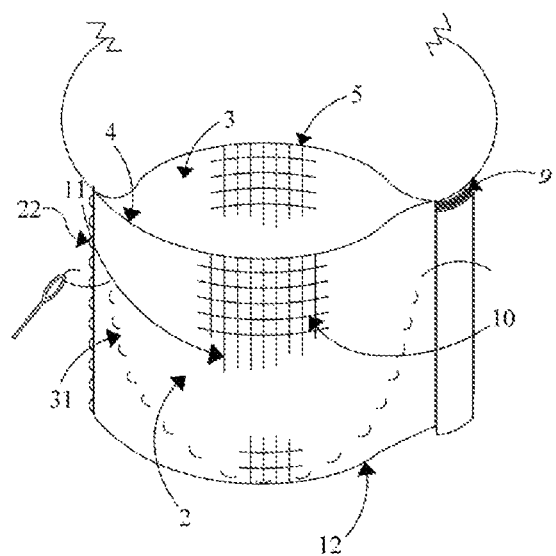

In a another step, as depicted in FIG. 1F, an additional stitch 31 is added, for example following a U-shaped line, which stitch further connects sections of layer 3 and corresponding sections in layer 2, to better define the leaflets or make a 3D-like shape. A segment of the tubular structure showing one combination of supporting element and leaflet is shown in FIG. 1F. As can be seen, the free margin of the leaflet is formed by selvedge 5. The connections made comprise, starting from the free margin, stitch 22 and stitch 31. Stitches 22 and 31 can also be continuous, i.e. stitches 22 may not extend over the full height of the valve, but may deflect and continue forming the U-shaped curve of stitches indicated as 31. This way, the leaflet and supporting element together form a pocket. By taking a position adjacent the supporting elements, the leaflets may open the ultimate valve, and by taking a position that extends away from the supporting elements, the leaflets may close the ultimate valve.

Figure 1G:
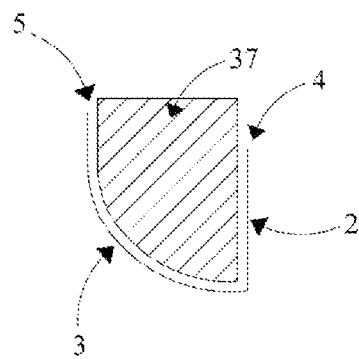

Referring now to FIG. 1G, in order to even better shape the leaflet and pocket, a mold 37 may be used. Before stitching connecting line 31, mold 37 may transpose the leaflet into shape, optionally by pulling the leaflet at edge 5 upwardly. This way, extra length is created between the nadir and the centre of the valve along the leaflet. Another way of creating such extra length is to already weave a larger (sections in) layer 3 than in layer 2, by using more warp yarns in layer 3 than in 2. The steps as illustrated by FIGS. 1F and 1G can also be performed during or after connecting to a stent.

Figure 1H:
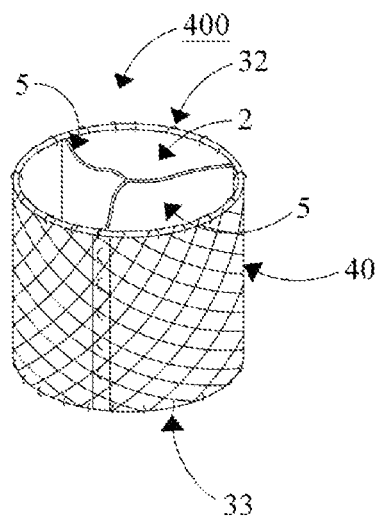
Figure 1I:
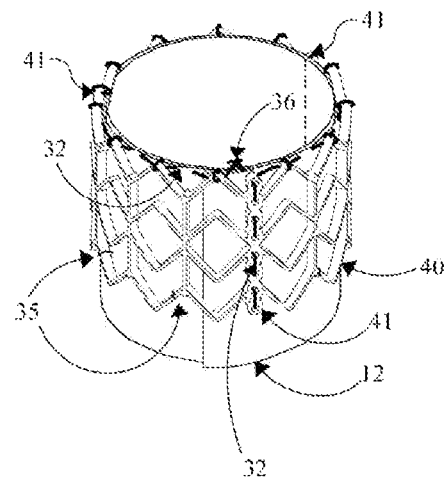

Referring now to FIGS. 1H and 1I, the textile structure or leaflet assembly made is connected to a circular wire stent 40 to make valve 400. The leaflet assembly is placed within the stent and may be stitched at its bottom to the stent with stitches 33, and at the top with stitching 32 connecting supporting elements 2. This stitching 32 preferably continues to connect the leaflets and supporting elements with the three stent posts 41 (see FIG. 1I), such connection further forming the final commissure. The free margins 5 of the three leaflets are also depicted in FIG. 1H. In this form, the valve 400 is closed by coaptation of the leaflets in neutral position. Would the free margins 5 be adjacent the supporting element 2 (i.e. adjacent the wall of stent 40), the valve 400 would be open. Some more details of the stent configuration and its posts 41 are depicted in FIG. 1I. Knot 36 is made in suture 32, as connecting point for this suture after circumferentially connecting the fabric. In an alternative approach, stitches 33 may be made at this stage; than temporary connections 35 may be used to keep the structure in place during suturing to posts 41, and can be removed thereafter. FIG. 1I shows an alternate embodiment wherein the leaflet assembly extends from the bottom of the stent, and this part may in a further step be folded to the outside of the stent and connected thereto. An advantage hereof may be smoother fitting to a vessel or artery upon implantation.

In an alternative embodiment, instead of using stitches 22 early in the forming process (as shown in FIG. 1C), the double woven textile structure as such (as shown in FIG. 1B) is tightly wrapped around the stent 40 (the stent at this stage being covered with a protective sheet of plastic) or another shaping member like a rod, and the four layers of the closure 9 are sutured together. Thereafter the stent is removed carefully, and the tubular textile structure is placed inside the stent. Then, stitches (sutures) corresponding to stitches 31, 32 and 33 are provided in order to form the leaflet cusps and secure the textile structure to the stent.

Figure 2A:
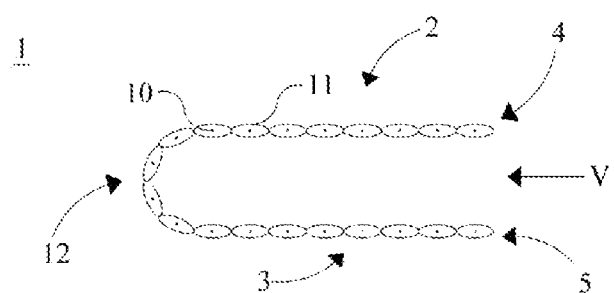
FIGS. 2A-2C schematically show various views of a textile structure suitable for making a valve prosthesis according to the invention.
Figure 2B:
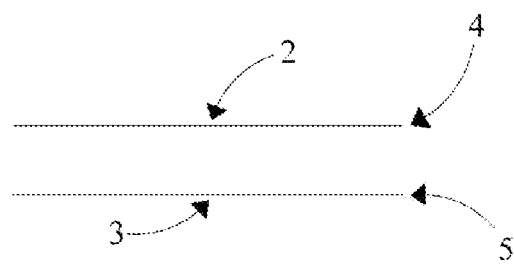
Figure 2C:
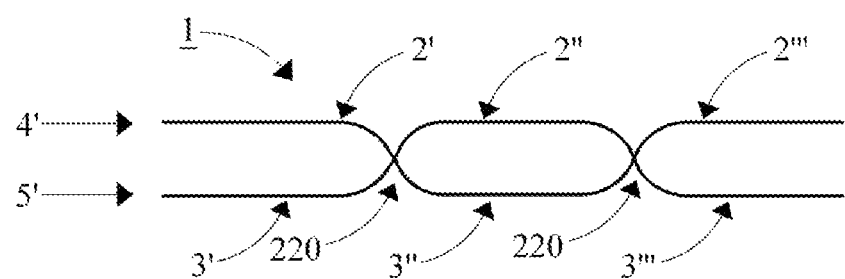

FIGS. 2A, 2B and 2C schematically show various views of a textile structure for making a prosthetic valve according to the invention. In the embodiment of FIG. 2A, across section parallel to the fill yarn of the textile structure 1 in the direction S, as shown in FIG. 1A, is given. As can be seen, the fill yarn 11 is interlaced in layers 2 and 3 with warp yarns 10 to form a plain weave. By using the double weave method as depicted in FIG. 1, both layers 2 and 3 have longitudinal (i.e. parallel to the warp yarns) selvedges 4 and 5 respectively. The fill yarn, at fold line 12 passes from layer 2 to layer 3 and vice versa, thereby forming part of the ultimate connections between leaflet and supporting element. In FIG. 2B, a side view of this textile structure in the direction V as indicated in FIG. 2A is given. In this view, only the selvedges 4 and 5 are schematically depicted.

In an alternative embodiment, as depicted in FIG. 2C and representing a similar viewpoint as in FIG. 2B, the fill yarn is interlaced with the warp yarns in such way that cross lines 220 are formed in the textile structure. The textile structure 1 now comprises in total 6 sections in the two layers, viz. sections 2', 2" and 2''' in the top layer and sections 3', 3" and 3''' in the bottom layer. At the left cross line 220, the four sections 2', 2", 3' and 3" coincide along a line that will correspond to (part of) the commissure of the ultimate valve. For this, warp yarns pass from section 2' to section 3" and warp yarns pass from section 3' to section 2", as controlled during weaving by the moving pattern of heddles and warp yarns. This way not only a mutual configuration is obtained wherein each section corresponds with a supporting element or leaflet, but also, a leaflet-supporting element connection is formed as a direct result of the weaving process, and has similar strength as the fabric itself. This also means that less (or even no) stitches need to be added to form the ultimate commissure, including attaching to a stent. A corresponding weaving process takes place at the right hand cross line 220. By connecting the ends of the structure obtained as depicted in FIG. 2C a tubular three-leaflet structure is obtained.

Figure 3A:
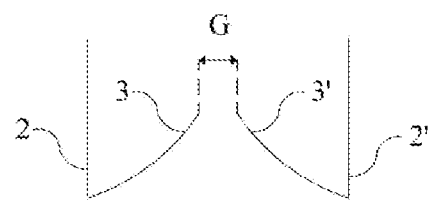
FIGS. 3A-3C schematically show the imposed geometry according to the present invention when compared to the prior art.
Figure 3B:
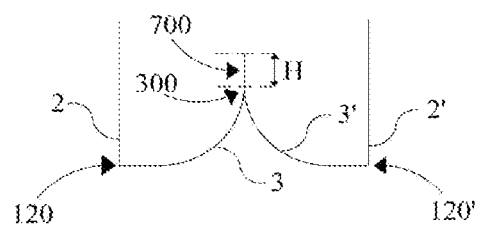
Figure 3C:
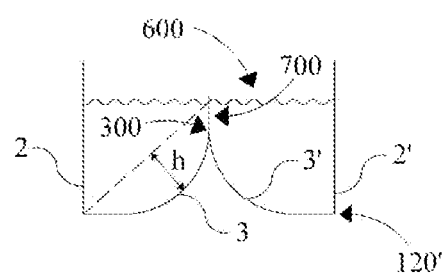

FIGS. 3A, 3B and 3C schematically show the imposed geometry according to the present invention, and a geometry according to the prior art. In each of the schematic drawings cross sections through the central line of a valve with two opposing leaflets 3 and 3' are depicted in closed, but neutral position without load, which leaflets are attached to their respective supporting element 2 and 2', in the depicted cross section at respective nadirs 120 and 120'. Note that for a valve with three leaflets the plane through the central line of one leaflet may have an angle of 60 degrees with the central plane of the opposite leaflet. FIG. 3A shows the imposed geometry of two leaflets, without pulsatile load, when made e.g. according to the method of Heim (see *Materials and Manufacturing Processes* reference as mentioned here above). At the center of the valve, there is a substantial gap G in neutral position without load. This gap will close and further open under pulsatile load by extending the leaflet material (about 15%, partly due to stretch of the polyester yarns, partly due to a rearrangement of the yarns in the textile), mimicking the dynamics of a natural valve. The radius of curvature of the leaflets is around 50 mm without pulsatile load.

FIG. 3B shows a cross section of a leaflet assembly in a prosthetic valve according to the invention. The opposing leaflets 3 and 3' have an imposed geometry in neutral position without pulsatile load that makes them abut each other along the length of the free margin, thus also at the centre of the valve, and therewith form a coaptation 700 with a coaptation height H at this cross section. The coaptation height H in this embodiment is 6 mm at the centre and extends with a minimum of 0.1 mm (the bottom of which is indicated with reference number 300) over the length of the free margin of each of the leaflets, possibly being even larger towards the commissures depending on commissure length. The geometry also comprises per leaflet a convex surface that extends between the top of the closure surface H and the respective connections to supporting elements, of which nadirs 120 and 120' are shown in the cross section of the valve in FIG. 3B. Each convex surface bulges away from the respective supporting elements 2 and 2'.

In FIG. 3C it is shown that by a slight hydrostatic pressure, created by filling the pockets with water 600 as indicated, the imposed geometry and the coaptation height including formation of a closure "ribbon" having the length of the free margins can be inspected more easily and its dimensions estimated. It is noted that due to excess length of the free margin (more textile length then actually needed to span the distance between supporting elements and to coapt), it might be that at some spots when closing the valve by filling it with water, there is a wrinkle or small opening (a channel) in the closure surface. Such opening however is not persistent and will be closed in actual use by pulsatile. The curvature of a leaflet may also be characterized by a curvature height h, defined as the largest orthogonal distance between the centre line and a straight line connecting the free margin at the centre of the valve and the nadir.

Figure 4A:
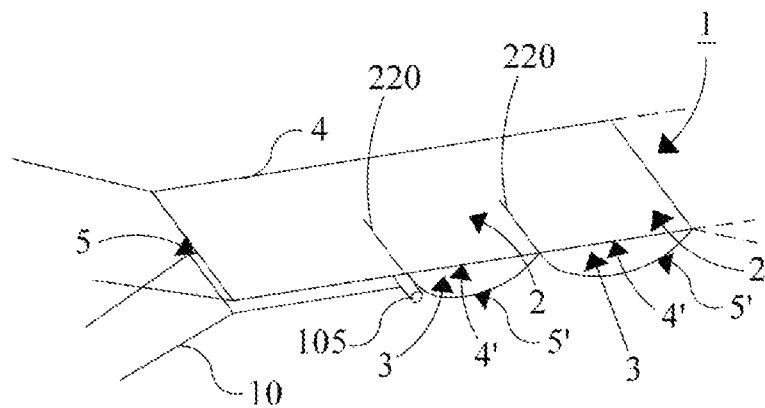
FIGS. 4A-4B schematically show various steps in a variant of the method as described in conjunction with FIGS. 3A-3C.
Figure 4B:
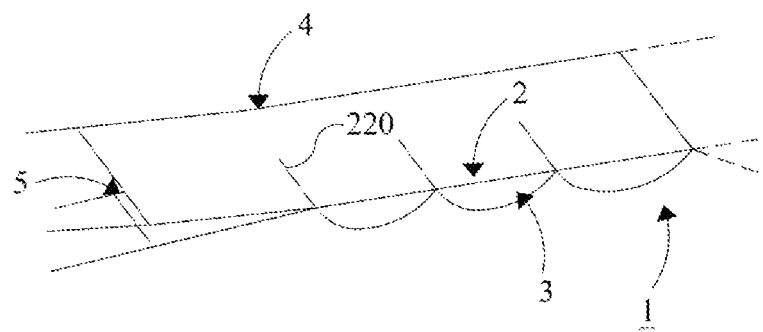

FIGS. 4A and 4B schematically show a continuous structure produced according to another embodiment, in line with the method as described in conjunction with FIG. 2C. In this embodiment a textile structure 1 is woven with two fill yarns, one for each layer, so that the top and bottom layers 2 and 3 have a selvedge at both sides (4, 4', 5 and 5'). Layer 2 is larger in width direction than layer 3 by using more warp yarns; note that only at the edges warp yarns 10 are depicted for both layers. In the resulting leaflet assembly the supporting element will thus be longer and extend away from the leaflets; and thus can be used for example to fold around a stent. The selvedges 5 or 5' may form the free margin of the leaflets in the resulting valve. In an alternative embodiment, the extending supporting element layer can be used to attach the leaflet assembly to the wall of a vessel or artery, thus functioning as a graft to (partly) replace or reinforce a weak or aneurysmal vessel. Such leaflet assembly, also without a stent, can thus function as a valve and as a graft, and may be called a valved graft or grafted valve. In such embodiment the outside of the leaflet assembly, the supporting elements layer, may be further treated to reduce permeability, e.g. by providing a coating or a further layer of material.

The bottom layer is extended with extra fill yarns to increase the size of the (free margin of the) leaflet. When the desired extra length for the leaflets is reached, layer 3 is pulled back with retaining bar 105 so that the fill line of the top layer is in line with the bottom layer as shown in FIG. 4A. The warp yarns of the bottom layer and the corresponding part of the warp yarns of the top layer are than crossed to form cross line 220; also shown in FIG. 4B. These cross lines provide that a commissure at least for the length formed by cross lines 220, starting at the free margin runs in parallel with the longitudinal axis in the ultimate valve formed out of structure 1 (corresponding to the method as outlined in FIG. 1). After weaving, the product may be cut into desired lengths, and connected to form a tubular structure, and optionally connected to a stent.

Alternatively, leaflets may be made to be larger than supporting elements. In a further alternative way, a fold line is formed at one edge by crossing fill yarn to the other set of warp yarns.

Figure 5:
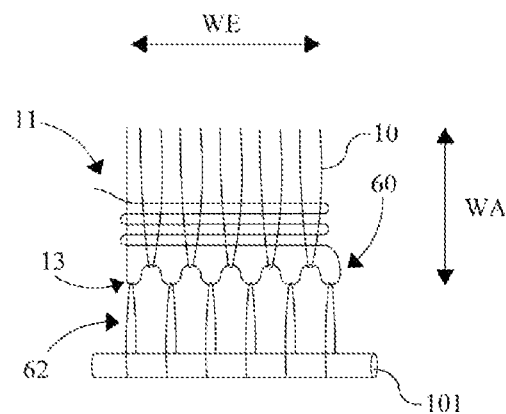
FIG. 5 schematically shows how a selvedge can be woven in an edge perpendicular to the warp direction.

FIG. 5 schematically shows how a selvedge can be woven, even in an edge perpendicular to the warp direction WA. In this case, connected to the warp beam 101 is a stay, comprising multiple hooks 62. The warp yarns 10 each form a loop, and each of these loops is connected to the beam using the hooks of the stay, which thus extends between the warp beam 101 and the said loops. The fill yarn 11 is interlaced with the warp yarns 10 in fill direction WE. In this particular embodiment a cord 60 is used to fix the said loops to the hooks 62. For this, the cord 60 extends along the margin 13 through each loop of the warp yarns, and is connected to the warp beam using the stay as indicated here above. In this case, the cord 60 is a section of a warp yarn and further continues as the fill yarn 11, so no loose ends are adjacent edge 13. Using this method the warp yarns at the margin 13 form a loop, and thus are continuous at this margin, which is thus formed as a selvedge. The selvedge in this case extends in the fill direction WE, perpendicular to the warp direction WA. The resulting flat fabric has thus at least selvedges at three of its edges. This way of forming a selvedge in warp threads can also suitably be used in forming non-flat but e.g. tubular textile structures, wherein this edge or margin corresponds to the free margin of the leaflet of the ultimate valve. Examples of such tubular textile structures are schematically depicted in the following figures.

In another embodiment, the hooks connect the warp beam directly to loops of the warp yarns. To prevent a free end of the fill yarn, it is preferred to loop the fill yarn around one of the warp yarns (advantageously a yarn near a side of the weave if the weave is a flat weave) and thereafter weave using the two ends of the fill yarn as individual fill yarns.

It was found that use of UHMWPE yarns as fill yarn was particularly advantageous when preparing a woven fabric with a selvedge parallel to the fill yarns as the yarns tended to adjust transversely, to fill the loops of the warp yarn when stay or hooks were removed. It could be theorized (without wishing to be limited thereto) that this surprising finding for a yarn with very high strength and modulus, is related to the combination of the low friction coefficient of UHMWPE and bending flexibility of UHMWPE yarns.

FIGS. 6A through 6F schematically show various steps in another embodiment, in which method a tubular (endless) woven textile structure is used for making a leaflet assembly for a valve.

Figure 6A:
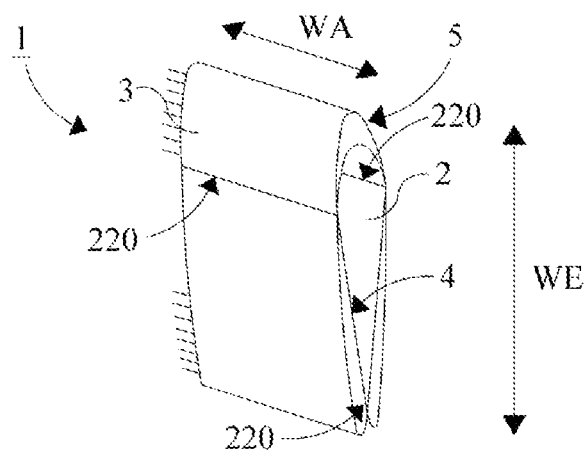
FIGS. 6A-6F schematically show various steps in another embodiment of a method according to the invention.
Figure 6B:
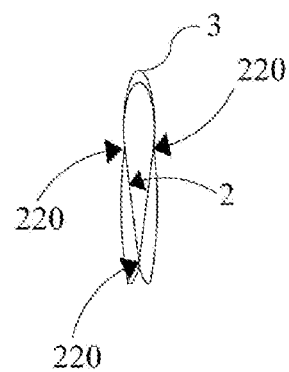
Figure 6C:
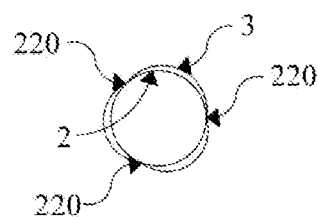
Figure 6D:
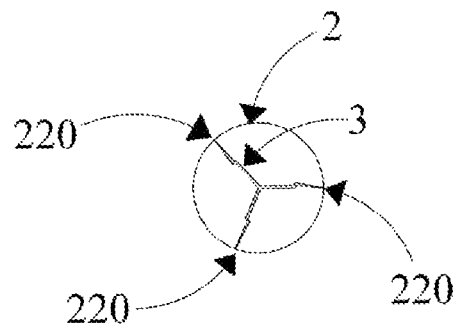
Figure 6E:
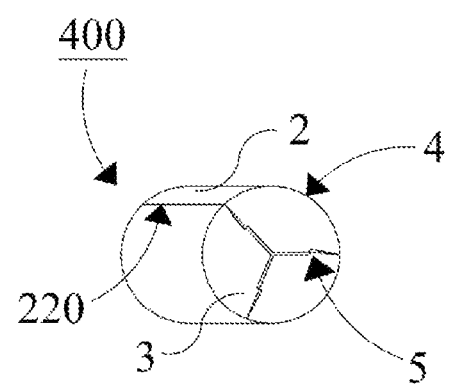

FIG. 6A (warp direction is indicated as "WA", fill direction as "WE") shows a woven tube-like textile structure 1 consisting of inner tubular layer 2, corresponding to the supporting elements of the ultimate valve as depicted in FIG. 6E, and outer layer 3 having three sections, which will correspond to leaflets having excess length in the free margins. The outer and inner layer are connected along three lines 220. In this embodiment the inner tubular layer 2 has selvedges 4 and the layer 3 has selvedges 5, a textile structure resulting from e.g. the method described in FIG. 5 using a warp beam of specific design. Alternatively, such structure is made in a continuous weaving process, followed by cutting to desired lengths and making stabilised edges. The leaflet sections in layer 3 are connected to the supporting elements in layer 2 via cross lines 220 (corresponding to cross lines 220 as depicted in FIG. 2C, albeit that in this case the fill yarns cross, whereas in FIG. 2C the warp yarns cross).

FIG. 6B gives a top view (or cross sectional view) of the textile structure of FIG. 6A (in warp direction). FIG. 6C gives the same view, but with the textile structure from its original flattened form now being configured such that layer 2 forms a circular tube. The leaflet sections of layer 3 extend over the surface of this tube and meet at the cross lines 220. In a next process step the textile structure of FIG. 6C is turned inside out, which leads to a structure as depicted in FIG. 6D. At this stage, the textile structure is processed such that the supporting elements 2 are on the outside, and the leaflets 3 are on the inside, thus forming a leaflet assembly or valve 400 as shown in FIG. 6E in an isometric view (in closed valve configuration).

Figure 6F:
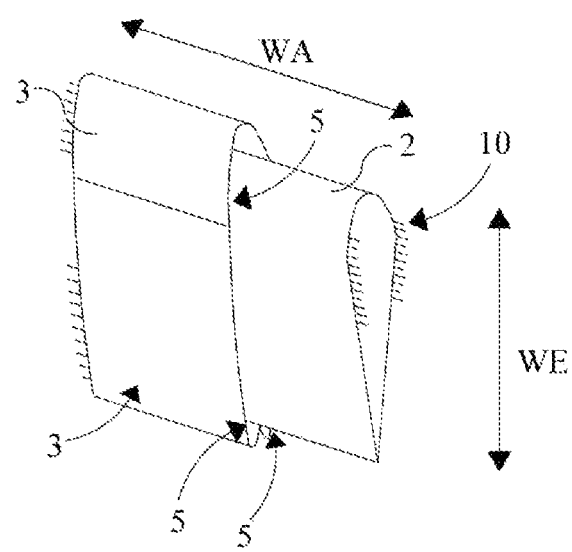

In FIG. 6F an alternative embodiment of a textile structure using a method similar to that described above is schematically depicted, in which embodiment layer 2, unlike the structure as shown in FIG. 6A, extends over a longer distance than the layer 3. In this embodiment, the margin 5 of the leaflet section(s) in layer 3 is formed as a selvedge (for example using a circular warp beam and using a method as depicted in FIG. 5), and the margin of layer 2 is woven as a regular edge wherein the warp yarns are discontinuous at the edge (for example discontinuous since they are cut to release the structure from the loom). For simplicity only some ends of warp yarns 10 are depicted, similarly to FIG. 6A. This textile structure can be formed into a valve the same way as the structure of FIG. 6A, that is by inverting. An advantage of the resulting leaflet assembly is that the supporting element is longer, extending away from the actual leaflets, and thus can be used for example to connect to the outside of a stent used in making a prosthetic valve or to attach the leaflet assembly to an artery as a valved graft. Similarly layer 2 may extend at the opposite end of the structure, or layer 3 may be made larger.

The invention will be further elucidated by the below exemplary experiments.

Example 1

This example describes making a prosthetic valve according to the invention, and experiments wherein such valve is tested in vitro and used as a pulmonary valve prosthesis by implanting in sheep. In this example, each valve is made with the method described below, which is basically corresponding to the method as described in connection with FIG. 1 and FIG. 3B.

A woven fabric as shown in FIG. 1B was made from Dyneema Purity® TG 10 dtex UHMWPE multifilament yarn (available from DSM, The Netherlands) with a density of 458 warp yarns per inch and 223 fill yarns per inch. The folded two-layer structure had a length of 90 mm and a width of 21.5 mm, a layer thickness of 0.00314 inches (80 μm), and was woven as a 2 by 2 twill weave, with longitudinal selvedges. The cylindrical stent used has the design as shown in FIG. 1I, and was made of electromagnetically polished stainless steel 304. It had an outer diameter of 25 mm, an inner diameter of 23 mm and a height of 17 mm. For the stitches, two kinds of suture thread was used: Maxbraid PE 3-0 suture blue with tapered needles (available as MPC 900252 from BIOMET MERCK LTD), here beneath referred to as Suture A, and Maxbraid PE 4-0 suture blue with tapered needles (available as MPC 900244 from the same supplier), here beneath referred to as Suture B. Both sutures comprise UHMWPE yarn.

The pulmonary valve was made as follows. In order to create a coaptation height of 6 mm over the length of the free margins of the leaflets, extensive free margin length was created. The free margin length was oversized by following steps:

1. The leaflet free margin length in the textile structure as woven will be inherently equal to the supporting element length, the two layers having the same length. The distance between the edge of the supporting element formed as a cylinder and the middle of the valve being its radius R, the total length needed for 3 leaflets bridging this distance is 6 R, whereas the length of the supporting element is 2 πR. This creates an inherent excess length factor for the leaflet of 2 πR/6 R=1.05.
2. The two layer woven fabric is initially wrapped around (i.e. to the outside of) the 25 mm stent and the ends perpendicular to the free margin of the leaflets are sutured together. Subsequently the cylindrical textile structure is placed inside the stent of inner diameter 23 mm and fixed to the stent with UHMWPE sutures. This creates an excess length factor of 25/23=1.09.
3. In this example the final prosthetic heart valve size is 23 mm for implantation, therefore the stent of 25 mm outer diameter is radially compressed to 23 mm. This way the inside diameter of the stent where the supporting element and leaflet is fixed to is reduced from 23 mm to 21 mm. This creates an excess length factor of 23/21=1.10.

The total excess length factor of leaflet free margins created this way is π×25/3×21=1.25. The excess length thus created is about 25%.

As indicated here above, the woven fabric is tightly wrapped around the stent, initially being used as mold, and the four layers at the closure (corresponding to 9 in FIG. 1D) are sutured together with Suture A starting at the outflow side of the fabric/stent combination by creating a knot 36, leaving about 2 cm loose end and a long end which is used to create a stitch line towards the inlet side of the fabric/valve combination. The stent/mold is removed carefully, and the tubular textile structure is placed inside the stent. The orientation of the warps of the leaflets and supporting element are perpendicular to the longitudinal central axis of the stent and commissural stent posts, ergo the fill yarns are in parallel to the central axis and commissural stent posts. The Suture A is then guided across fringe and stent post holes from inlet side towards outlet side (as shown in FIG. 1I), thus fixing the stent post 41 to the supporting element and leaflet at a length of about 9 mm. At the top of the post (outflow side) suture A is used to fix the edge of the supporting element to the stent in a continuous way by taking locked bites at the bended ends of the stent (the commonly known "Method of Blalock" using a festooning suture line). The end of the suture A is tied to its beginning at knot's 36 loose end. The textile structure is temporarily fixed to the remaining commissural stent posts 41 in a 120 degree fashion thus dividing it in three parts with about the same free margin length, to keep the structure in place during next steps; after which the temporary fixations can be removed.

A second suture B is used to complete attaching of the textile structure and create the actual leaflet assembly within the stent, by stitching to the two remaining stent posts 41 with a length of about 9 mm, and by stitching leaflet layer to the supporting element layer and stent to create the valve cusps. Prior to suturing, the free margin of all three individual leaflets were pulled up 3 mm in the middle of the free margin at the expense of length of the supporting element at the inflow side thus creating an arch of woven fabric between commissural posts elevated over the plane of the stent outflow side. Together with the aforementioned excess length this results in about 6 mm coaptation height in the center of the heart valve, and is likely even higher towards the commissures of about 9 mm. A mold (a negative form taken from a human aortic valve) is used for further sizing and shaping the belly of the leaflet as shown in FIG. 1G. The leaflet assembly is temporarily sutured (35) in the middle between the posts at the inflow side to maintain this configuration during next step. From this point suturing is started according to FIG. 1I. At the top of the post the leaflet and supporting element are taken double with two encircling bites. The leaflet sheet is pulled a little bit backwards over the top of the stent and is fixed by the suture. The course of the suture line of the leaflets (U-shaped) is also guided by the shapes of the stent and mold. The end of the suture is tied to the loose end left at the knot of the beginning of suture B. The resulting leaflets had a convex surface at the centre line of these leaflets with a radius of curvature of about 12 mm without pulsatile load. This was estimated to represent a distance h as depicted in FIG. 3C along the centre line with a height h of about 5 mm. The textile structure extends a few millimetre from the stent at the inflow site, as also shown in FIG. 4I, which can be used to attach the valve to vessel or artery wall upon implantation. The leaflet assembly is further connected with sutures to the lower part of the stent, and the temporary sutures 35 are removed.

After this fixation of leaflet assembly, the stent 40 of the valve is compressed from 25 mm diameter to 23 mm diameter and sterilized by using ethylenoxide sterilization.

Performance of valves made as described above was tested both in vitro and in vivo. Mechanical and functional testing of the prosthetic heart valve was performed in a simplified mock circulation. A BVS 5000 circulatory assist device (Abiomed, Danvers, Mass., USA) was included in a closed loop circuit having a reservoir and a return conduit. The heart pump bladder was driven by an Intra Aortic Balloon Pump (Maquet, Rastatt, Deutschland) with a frequency of 80 beats/min and output of 3600 cc/min, while afterload at the outflow side of the heart pump was set to 80 mmHg using a water column. In an initial test the standard valve of the heart pump at the outflow side was replaced by a valve constructed with three single leaflets made from woven fabric of 55 dtex UHMWPE yarn mounted in a transparent plastic conduit to study its open and closure behavior. This pilot valve sustained >4 weeks (3.571.200 cycles) while competent without deterioration of the woven leaflets. Build on this experience, a valve constructed as above (based on leaflets from woven fabric of 10 dtex UHMWPE yarn), was tested under equivalent physiologic loading conditions of the systemic human circulation, cumulatively during over 120 days (13.824.000 cycles). The valve opened fully into an optimal effective orifice, having commonly known vertical position of vibrating leaflets in parallel to the fluid stream, and closed while visually not revealing closure defects along the coaptation line of meeting free margins of leaflets, except from a tiny central hole of about 0.5 mm. Visual inspection after testing revealed a completely intact valve geometry; leaflets showing no fraying at the free margin or any other disruption or defects. All the suture lines as described above, as well as the knots were intact.

The prosthetic pulmonary valves were also implanted in adult sheep models (bread "swifter", body mass 55-70 kg) on the beating heart, while using an extra-corporeal circulation machine. Access to the pulmonary artery was achieved through left thoracotomy 3rd-4th i.c.s. The pulmonary artery was incised longitudinally, whereafter the native leaflets were cut out. Three positioning stitches of 5-0 Prolene® were used to pull on the commissural native posts. The valve was sutured into the pulmonary artery on the supra annular level (plane top of native commissures) using 5-0 Prolene®. The pulmonary artery was closed in linear fashion.

Echocardiography showed normal leaflet function without valvular or paravalvular regurgitation, apart from some occasional minimal regurgitation in the centre of the valve. The wound was closed and the sheep was taken to stables for recovery.

The sheep remained stable, without any adverse clinical signs up to 6 months observation periods. After this period the leaflet function was assessed again. Echocardiography showed adequate leaflet function with minor to moderate valvular but no paravalvular regurgitation, and there was no change in effective orifice since the day of implant. After this, the valves were taken out of the sheep for inspection. The leaflets and supporting elements were overgrown with tissue, but this appeared to be a very thin layer of fibroblasts and endothelial cells without histological and radiological signs of tissue calcification, and with a maximum thickness (including the leaflet) of 250 µm at the free edge with increasing amount of streamlining repair tissue towards the nadir. The mechanics of the valve appeared to be unaltered, all sutures were in place without fractures and the free margin of the leaflets appeared to be completely intact as originally made. No signs of fraying or other anomalies could be detected. The inventors are not aware of other studies using a prosthetic valve having leaflets made from a fabric woven from synthetic fibers, and wherein animals having such implanted valve survived a 6 months period without complications.

Example 2

A prosthetic aortic valve to be implanted in the systemic circulation was made analogously to Example 1 with some modifications. The supporting element was prepared by taking out three half-moon pieces of fabric (facing the sinus valsalva in the human or animal aorta) to allow blood supply to flow into the coronary ostia. The remaining edge of the supporting element was fixed to the leaftlet according to corresponding suture line of the U-shaped cusp suture line (facing the sinus valsalva). A second suture was used to complete attaching of the textile structure and create the actual leaflet assembly within the stent, by stitching to the stent posts 41 with a length of about 9 mm, and by stitching the leaflet layer to the supporting element layer and stent to create the valve cusps.

The valve was subsequently constructed in similar way as the pulmonary valve described here above. When completed, an additional sewing cuff of braided UHMWPE yarn was sutured with MaxBraid™ 3-0 UHMWPE (available from Teleflex, Limerick, Ireland), in an everted fashion using the Blalock stitch configuration.

Valves were implanted in adult sheep models (bread "swifter", body mass 65 kg) on the arrested heart under support of extra-corporeal circulation. Access to the aortic root was achieved through left thoracotomy 3rd-4th i.c.s. The pulmonary artery was dissected and pulled aside to allow transverse incision of the aorta. Classical implant was performed under cardiac arrest using a running suture Prolene® 5-0. The aorta was closed with a pericardial patch and the heart was defibrillated thereafter. The heart lung machine was disconnected. Echocardiography showed normal leaflet function without valvular or paravalvular regurgitation.

Example 3

A valved conduit or valved graft was constructed from a single piece of flat sheet of chemically prepared porcine intestine submucosa (CorMatrix®, Roswell, US). In a series of chronic sheep and lamb, valves having a diameter 25 and 18 mm, respectively, were implanted as an interponate graft between the outflow tract of the right ventricle and the distal main pulmonic artery. The surgical access was the same as described in Example 1 and implant was performed using extra-corporeal circulatory support. The pulmonic artery was cross sectioned above the pulmonic valve that was removed subsequently.

For a 25 mm diameter conduit/valve a trapezoid shaped sheet was prepared having one width of approximately 12 cm (A) and one of 14 cm (B) and having two sides (C and D) with lengths greater than 10 cm. From the flat sheet a conical tube was constructed by suturing together the free slant sides C and D with a festooning 4-0 Prolene® suture in an everted way. Excess material was cut away and the tube was folded and inverted in such way that the tubular part with larger circular edge B became positioned within the tube with circular edge A (outflow side) and leaving a folded rim at the inflow side. The circular edge B, forming the free margin of the leaflets was divided in three parts having the same length and subsequently fixed with a pledget armed suture (Prolene 4-0) to the outer tube at 120° each. Herewith, three commissures of 3-4 mm in the longitudal direction of the valve were created, and the three individual leaflets having excess length in their free margins coapted with at least 7 mm coaptation height without load. At the outflow side of A a cuff remained, which was used to connect the valve during implantation to the transected pulmonic artery. The inflow side of the tube having the folded rim was connected to the pulmonic artery stump. Once implanted, echocardiography showed normal leaflet function without valvular incompetence apart from some occasional minimal regurgitation in the centre of the valve.

Any one of the embodiments, aspects and preferred features or ranges as disclosed in this application and relating to a method of making a prosthetic valve or a valve as obtained with the method may be combined in any combination, unless otherwise stated herein or if technically clearly not feasible to a skilled person. The invention is further summarized in the below set of embodiments.

A prosthetic valve (400) comprising a leaflet assembly having at least one leaflet (3) attached to a supporting element (2), which leaflet has a free margin (5) that can move between a first position wherein the free margin is flexed away from a closure surface (700) to allow body fluid to flow through the valve, and a second position wherein the free margin abuts the closure surface to close the valve, and wherein the leaflet, without pulsatile load on the valve, can form a coaptation height of more than 0.1 mm along the length of the free margin.

The prosthetic valve according to previous embodiment, wherein the coaptation height is between 1 and 15 mm, preferably between 3 and 10 mm, more preferably between 5 and 7 mm.

The prosthetic valve according to previous embodiments, wherein the leaflet has a geometry comprising a convex surface with a radius of curvature at the centre line of the leaflet of 1, 2, 3, 4, 5, 6, 7, 8, 9, 10, 11, 12, 13, 14, 15, 16, 17, 18, 19 or 20 mm.

The prosthetic valve according to previous embodiment, wherein the radius of curvature is between 1 and 20 mm, preferably about 12 mm.

The prosthetic valve according to any one of previous embodiments, wherein the leaflet has a geometry comprising a convex surface, and having a curvature height, the largest orthogonal distance between the centre line and a straight line connecting the free margin at the centre of the valve and the nadir, of more than 1 mm, preferably more than 2, 3, or 4 mm and at most 15, 14, 13, 12, 11 or 10 mm, and most preferably of about 5 mm.

The prosthetic valve according to any one of the previous embodiments, wherein the free margin of the leaflet has excess length relative to the theoretical length needed for closing the valve, preferably the excess length is at least 7%, preferably between 10% and 40%, or between 15% and 30%.

The prosthetic valve according to any one of previous embodiments, wherein the leaflet is attach to the supporting element along a commissure that runs in parallel with the longitudinal axis of the valve starting at the free margin, preferably the commissure has a length of at least 1 mm and at most 9 mm, preferably 1-6 mm.

The prosthetic valve according any one of previous embodiments, wherein the leaflet comprises an elastic sheet material having an elongation at break of 10% or less, preferably less than 9, 8, 7, 6, 5, 4, 3, 2 or even 1%.

The prosthetic valve according to any one of previous embodiments, wherein the leaflet comprises a textile structure comprising one or more elastic yarns having an elongation at break of 10% or less, preferably of less than 9, 8, 7, 6, or 5%, more preferably of between 1 and 5%.

The prosthetic valve according to previous embodiment, wherein the textile structure is a woven fabric made from the one or more elastic yarns, and preferably the woven fabric comprises plain, twill or basket weave patterns.

The prosthetic valve according to previous embodiment, wherein the textile structure is a single piece of woven fabric, preferably a single piece of woven fabric comprising multiple stacked layers.

The prosthetic valve according to previous embodiments, wherein the free margin of the leaflet is a selvedge of the woven fabric.

The prosthetic valve according to previous embodiments, wherein the textile structure is a multilayer woven fabric comprising stacked layers, which layers are interconnected, preferably by crossing warp or fill threads, at desired locations to define leaflets and supporting elements.

The prosthetic valve according to previous embodiments, wherein the woven fabric is a two-layer fabric that comprises two selvedges at an open side, and a continuous fold line at the opposite closed side.

The prosthetic valve according to previous embodiments, wherein the woven textile structure is a seamless tubular fabric, optionally a multi-channel or multi-layer tubular fabric.

The prosthetic valve according to previous embodiments, made by continuously weaving the textile structure, subsequently cutting the resulting structure into desired lengths, and optionally stabilising the cut edges.

The prosthetic valve according to previous embodiments, wherein the elastic yarn has a linear density of less than 120 dtex, preferably a linear density of less than 60 dtex, preferably between 5 and 30 dtex, more preferably between 7 and 15 dtex.

The prosthetic valve according to previous embodiments, wherein the thickness of a layer of the textile structure, preferably a woven fabric, is 20-200 µm, preferably between 40 to 150 µm, or between 50 to 100 µm.

The prosthetic valve according to previous embodiments, wherein the textile structure comprises polymeric filaments, preferably UHMWPE filaments, more preferably the textile structure comprises at least 80 mass % of UHMWPE filaments with a tenacity of at least 20 cN/dtex, more preferably the warp and the fill yarn consist essentially of UHMWPE filaments.

The prosthetic valve according to any one of previous embodiments, further comprising a stent (40) connected to the leaflet assembly.

The prosthetic valve according to previous embodiment, wherein the stent is connected by stitches, preferably by stitches made with a suture that has similar strength as a yarn in the leaflet assembly, more preferably by stitches made with the same type of yarn, or a by suture made therefrom.

The prosthetic valve according to any one of previous embodiments, wherein the valve comprises two leaflets, the second leaflet acting as the closure surface for the first leaflet and vice versa.

The prosthetic valve according to previous embodiment, wherein the valve comprises three leaflets, each leaflet acting as the closure surface for the other two leaflets.

The prosthetic valve according to any one of previous embodiments, being an implantable prosthetic heart valve.

A leaflet assembly for a prosthetic valve as described in any one of previous embodiments.

A method of making a prosthetic valve (400), the valve comprising a at least one leaflet (3) attached to a supporting element (2), which leaflet has a free margin (5) that can move between a first position wherein the free margin is flexed away from a closure surface (700) of the valve to allow a body fluid to flow through the valve, and a second position wherein the free margin abuts the closure surface to close the valve, the method comprising:
providing a sheet material,
forming a leaflet assembly comprising at least one leaflet and a supporting element from the sheet material, and
forming the valve therewith,
wherein forming the leaflet assembly comprises shaping the leaflet to impose a geometry wherein the leaflet, without pulsatile load on the valve, can form a coaptation height of more than 0.1 mm along the length of the free margin.

The method according to previous embodiment, wherein the coaptation height is at least 2, 3, 4 or 5 mm and at most 15, 13, 11, 10, 9, 8, or 7 mm.

The method according to previous embodiment, wherein the coaptation height is between 1 and 15 mm, preferably between 3 and 10 mm, more preferably between 5 and 7 mm.

The method according to any one of previous embodiments, wherein the geometry comprises a convex surface that has a radius of curvature at the centre line of the leaflet of 1, 2, 3, 4, 5, 6, 7, 8, 9, 10, 11, 12, 13, 14, 15, 16, 17, 18, 19 or 20 mm.

The method according to previous embodiment, wherein the radius of curvature is between 1 and 20 mm, preferably about 12 mm.

The method according to any one of previous embodiments, wherein the geometry comprises a convex surface, with a curvature height of more than 1 mm, preferably more than 2, 3, or 4 mm and at most 15, 14, 13, 12, 11 or 10 mm, and most preferably of about 5 mm.

The method according to any one of previous embodiments, wherein the leaflet is formed such that the free margin of the leaflet has excess length relative to the theoretical length needed for closing the valve, preferably the excess length is at least 7%, preferably between 10% and 40%, or between 15% and 30%.

The method according to previous embodiment, wherein the excess length is created by one or more of the method steps chosen from the group of preforming the sheet material as having a specific shape, for example by forming a trapezium-like sheet material or a tapered or conical tubular material, reducing the outer circumference of the valve, and shifting the leaflet surface before fixing the leaflet in the valve.

The method according to any one of previous embodiments, wherein the leaflet is attached to the supporting element along a commissure that runs in parallel with the longitudinal axis of the valve starting at the free margin, preferably the commissure has a length of at least 1 mm and at most 9 mm, preferably about 1-6 mm.

The method according to any one of previous embodiments, wherein the sheet material is an elastic material having an elongation at break of 10% or less, preferably less than 9, 8, 7, 6, 5, 4, 3, 2 or even 1%.

The method according to any one of previous embodiments, wherein the sheet material is a textile structure comprising one or more elastic yarns having an elongation at break of 10% or less, preferably of less than 9, 8, 7, 6, or 5%, more preferably of between 1 and 5%.

The method according to previous embodiment, wherein the textile structure is a structure woven from the one or more elastic yarns, and preferably the woven fabric comprises plain, twill or basket weave patterns.

The method according to previous embodiment, characterised in that the textile structure is a single woven structure, preferably a woven structure comprising multiple stacked layers.

The method according to previous embodiments, wherein the free margin of the leaflet is woven as a selvedge.

The method according to previous embodiments, wherein the textile structure is woven as a multilayer structure comprising stacked layers, which layers are interconnected, preferably by crossing warp or fill threads, at desired locations to define leaflets and supporting elements.

The method according to previous embodiments, wherein the textile structure is made by a double weaving process resulting in a two-layer fabric that has two selvedges at its open side, and a continuous fold line at the opposite closed side.

The method according to previous embodiments, wherein the textile structure is made by a double weaving process resulting in a seamless tubular fabric, optionally a multi-channel or multi-layer tubular fabric.

The method according to previous embodiments, comprising continuously weaving the textile structure, cutting the resulting structure subsequently into desired lengths, and optionally stabilising the cut edges.

The method according to previous embodiments, wherein the elastic yarn has a linear density of less than 120 dtex, preferably a linear density of less than 60 dtex, preferably between 5 and 30 dtex, more preferably between 7 and 15 dtex.

The method according to previous embodiments, wherein the thickness of a layer of the textile structure, preferably a woven fabric, is 20-200 µm, preferably between 40 to 150 µm, or between 50 to 100 µm The method according to previous embodiments, wherein the textile structure comprises polymeric filaments, preferably UHMWPE filaments, more preferably the textile structure comprises at least 80 wt-% of UHMWPE filaments with a tenacity of at least 20 cN/dtex, more preferably the warp and/or the fill yarn consist of UHMWPE filaments.

The method according to any one of previous embodiments, further comprising connecting the leaflet assembly to a stent (40).

The method according to previous embodiment, wherein connecting is done by applying stitches, preferably by using a suture that has similar strength as the yarn in the leaflet assembly, more preferably by using the same type of yarn, or a suture made therefrom.

The method according to any one of previous embodiments, wherein the valve comprises two leaflets, the second leaflet acting as the closure surface for the first leaflet and vice versa.

A method according to any one of the previous embodiments, wherein the valve comprises three leaflets, each leaflet acting as the closure surface for the other two leaflets.

A method for making a leaflet assembly for a prosthetic valve as described in any one of previous embodiments.

A leaflet assembly or a prosthetic valve as obtainable by the method according to any one of previous embodiments.

The invention claimed is:

1. A prosthetic heart valve that can take a first form wherein the valve is open and a second form wherein the valve is closed, the valve comprising:
    a leaflet assembly having three leaflets attached to a supporting element at respective first and second commissures, the leaflets having a free margin that can move between a first position wherein the valve takes the first form and a second position wherein the valve takes the second form with each leaflet acting as a closure surface for the other leaflets, wherein
    the leaflets can form a coaptation height in a longitudinal direction of the valve of between 1 and 15 mm along the free margin without a pulsatile load on the valve and without requiring substantial extension of the leaflets, wherein
    the free margin of each leaflet has excess length relative to a minimum length needed to bridge a distance between the end of the leaflet's free margin at the first commissure to the end of the leaflet's free margin at the second commissure via the center of the valve, and wherein
    the leaflets comprise an elastic sheet material having an elongation at break of 10% or less.

2. The prosthetic valve according to claim 1, wherein the coaptation height is between 3 and 10 mm.

3. The prosthetic valve according to claim 1, wherein the coaptation height is between 5 and 7 mm.

4. The prosthetic valve according to claim 1, wherein the leaflets comprise an elastic sheet material having an elongation at break of less than 6%.

5. The prosthetic valve according to claim 1, wherein elongation of the sheet material during use in the valve is less than 5%.

6. The prosthetic valve according to claim 1, wherein the leaflets comprise a textile structure comprising at least one elastic yarn having an elongation at break of 10% or less.

7. The prosthetic valve according to claim 6, wherein the textile structure is made by knitting, braiding or weaving the one or more elastic yarns.

8. The prosthetic valve according to claim 6, wherein the textile structure is a woven fabric made from the elastic yarn.

9. The prosthetic valve according to claim 8, wherein the woven fabric comprises plain, twill or basket weave patterns.

10. The prosthetic valve according to claim 8, wherein the free margins of the leaflets are a selvedge of the woven fabric.

11. The prosthetic valve according to claim 6, wherein the elastic yarn has a linear density of 5-120 dtex.

12. The prosthetic valve according to claim 6, wherein the elastic yarn has a linear density of at least 7-30 dtex.

13. The prosthetic valve according to claim 6, wherein the textile structure has a thickness of 20-200 μm.

14. The prosthetic valve according to claim 6, wherein the textile structure has a thickness of 50-100 μm.

15. The prosthetic valve according to claim 6, wherein the textile structure comprises ultrahigh molecular weight polyethylene (UHMWPE) filaments.

16. The prosthetic valve according to claim 6, wherein the textile structure is a woven fabric with warp and yarns consisting essentially of ultrahigh molecular weight polyethylene (UHMWPE) filaments.

17. The prosthetic valve according to claim 1, wherein the free margins have a length extending between first and second commissures, which length is at least 7% in excess relative to a theoretical length needed for closing the valve.

18. The prosthetic valve according to claim 1, wherein each leaflet is attached to the supporting element along commissures that run in parallel with a longitudinal axis of the valve starting at the free margin, the commissures having a length of at least 1 mm.

19. The prosthetic valve according to claim 1, further comprising a stent connected to the leaflet assembly.

20. A method of making the prosthetic valve according to claim 1 comprising:
    (i) providing a sheet material,
    (ii) forming a leaflet assembly comprising three leaflets and a supporting element from the sheet material, and
    (iii) forming the valve therewith, wherein
    forming the leaflet assembly according to step (ii) comprises shaping the leaflets to impose a geometry wherein the leaflets without pulsatile load on the valve and without requiring extension of the leaflets can form a coaptation height of between 1 and 15 mm along the free margin.

21. The method according to claim 20, wherein step (iii) comprises connecting the leaflet assembly to a stent.

* * * * *